(12) United States Patent
Sinclair

(10) Patent No.: US 11,738,067 B2
(45) Date of Patent: *Aug. 29, 2023

(54) ELEVATED INTRACRANIAL PRESSURE TREATMENT

(71) Applicant: INVEX THERAPEUTICS LTD., Subiaco (AU)

(72) Inventor: Alex Sinclair, Birmingham (GB)

(73) Assignee: INVEX THERAPEUTICS LTD., Subiaco (AU)

( * ) Notice: Subject to any disclaimer, the term of this patent is extended or adjusted under 35 U.S.C. 154(b) by 84 days.

This patent is subject to a terminal disclaimer.

(21) Appl. No.: 17/065,753

(22) Filed: Oct. 8, 2020

(65) Prior Publication Data

US 2021/0030848 A1 Feb. 4, 2021

Related U.S. Application Data

(63) Continuation of application No. 15/504,399, filed as application No. PCT/GB2015/052453 on Aug. 25, 2015, now Pat. No. 10,835,579.

(30) Foreign Application Priority Data

Sep. 3, 2014 (GB) ..................... 1415598

(51) Int. Cl.
| | |
|---|---|
| *A61K 38/17* | (2006.01) |
| *A61K 9/19* | (2006.01) |
| *A61K 9/00* | (2006.01) |
| *A61K 47/02* | (2006.01) |
| *A61K 31/495* | (2006.01) |
| *A61K 31/196* | (2006.01) |
| *A61K 31/75* | (2006.01) |
| *A61K 31/17* | (2006.01) |
| *A61K 38/14* | (2006.01) |
| *A61K 38/50* | (2006.01) |
| *A61K 31/475* | (2006.01) |
| *A61K 31/337* | (2006.01) |
| *A61K 31/282* | (2006.01) |
| *A61K 31/704* | (2006.01) |
| *A61K 38/26* | (2006.01) |
| *C07K 14/605* | (2006.01) |
| *C07K 14/575* | (2006.01) |
| *A61P 43/00* | (2006.01) |
| *A61P 25/00* | (2006.01) |

(52) U.S. Cl.
CPC .............. *A61K 38/26* (2013.01); *A61P 25/00* (2018.01); *A61P 43/00* (2018.01); *C07K 14/57563* (2013.01); *C07K 14/605* (2013.01)

(58) Field of Classification Search
CPC .......... A61K 38/26; A61P 25/00; A61P 43/00; C07K 14/57563; C07K 14/605
See application file for complete search history.

(56) References Cited

U.S. PATENT DOCUMENTS 8,853,160 B2 10/2014 Greig et al.

FOREIGN PATENT DOCUMENTS

| JP | 2003505413 A | 2/2003 |
| JP | 2008540336 B2 | 11/2008 |
| WO | WO-2001/007022 A2 | 2/2001 |
| WO | WO-2004/007446 A1 | 1/2004 |
| WO | WO-2007/027225 A2 | 3/2007 |

OTHER PUBLICATIONS

Bikash Manandhar, Glucagon-like Peptide-1 (GLP-1) Analogs: Recent Advances, New Possibilities, and Therapeutic Implications, Journal of Medicinal Chemistry, 58, 1020-1037, 2014.*
Beauchamp, K. et al., "Pharmacology of Traumatic Brain Injury: Where is the "Golden Bullet"?", Mol Med, vol. 14, No. 11-12, 2008, pp. 731-740.
Botfield, H.F. et al., "A glucagon-like pepide-1 receptor agonist reduces intracranial pressure in a rat model of hydrocephalus", Science Translational Medicine, vol. 9, eaan0972, 2017, pp. 1-12.
De Freitas Cardoso, M.G. et al., "Cognitive Impairment Following Acute Mild Traumatic Brain Injury", Frontiers in Neurology, vol. 10, Article 198, 2019, pp. 1-9.
Hiploylee, C. et al., "Intracranial pressure measured in freely moving rats for days after intracerebral hemorrhage", Experimental Neurology, vol. 255, 2014, pp. 49-55.
Rogatsky, G. et al., "Continuous Multiparametric Monitoring of Brain Activities Following Fluid-Percussion Injury in Rats: Preliminary Results", Multiparametric Responses to Brain Injury, vol. 7, No. 1, 1996, pp. 23-43.
Carney, N. et al., "Guidelines for the Management of Severe Traumatic Brain Injury 4th Edition", Brain Trauma Foundation, 2016, pp. 1-244.
Dunn, L.T. et al., "Raised Intracranial Pressure", www.jnnp.com, vol. 73 (Suppl. I), 2002, pp. i23-i27.

(Continued)

*Primary Examiner* — Julie Ha
*Assistant Examiner* — Erinne R Dabkowski
(74) *Attorney, Agent, or Firm* — Polsinelli PC

(57) ABSTRACT

Provided is an incretin, or analogue thereof, an incretin receptor agonist, an incretin enhancer, or any combination thereof, for use in a method of reducing elevated intracranial pressure (ICP) in a subject. Methods of reducing elevated ICP in a subject may comprise administering an incretin, or analogue thereof, an incretin receptor agonist, an incretin enhancer, or any combination thereof to the subject. The elevated ICP may be associated with idiopathic intracranial hypertension (IIH), secondary pseudotumour cerebri, hydrocephalus, normal pressure hydrocephalus, raised intracranial pressure secondary to a brain tumour, meningitis, brain trauma, brain injury, and venous sinus thrombosis.

22 Claims, 11 Drawing Sheets

(56) References Cited

OTHER PUBLICATIONS

Figure 1:
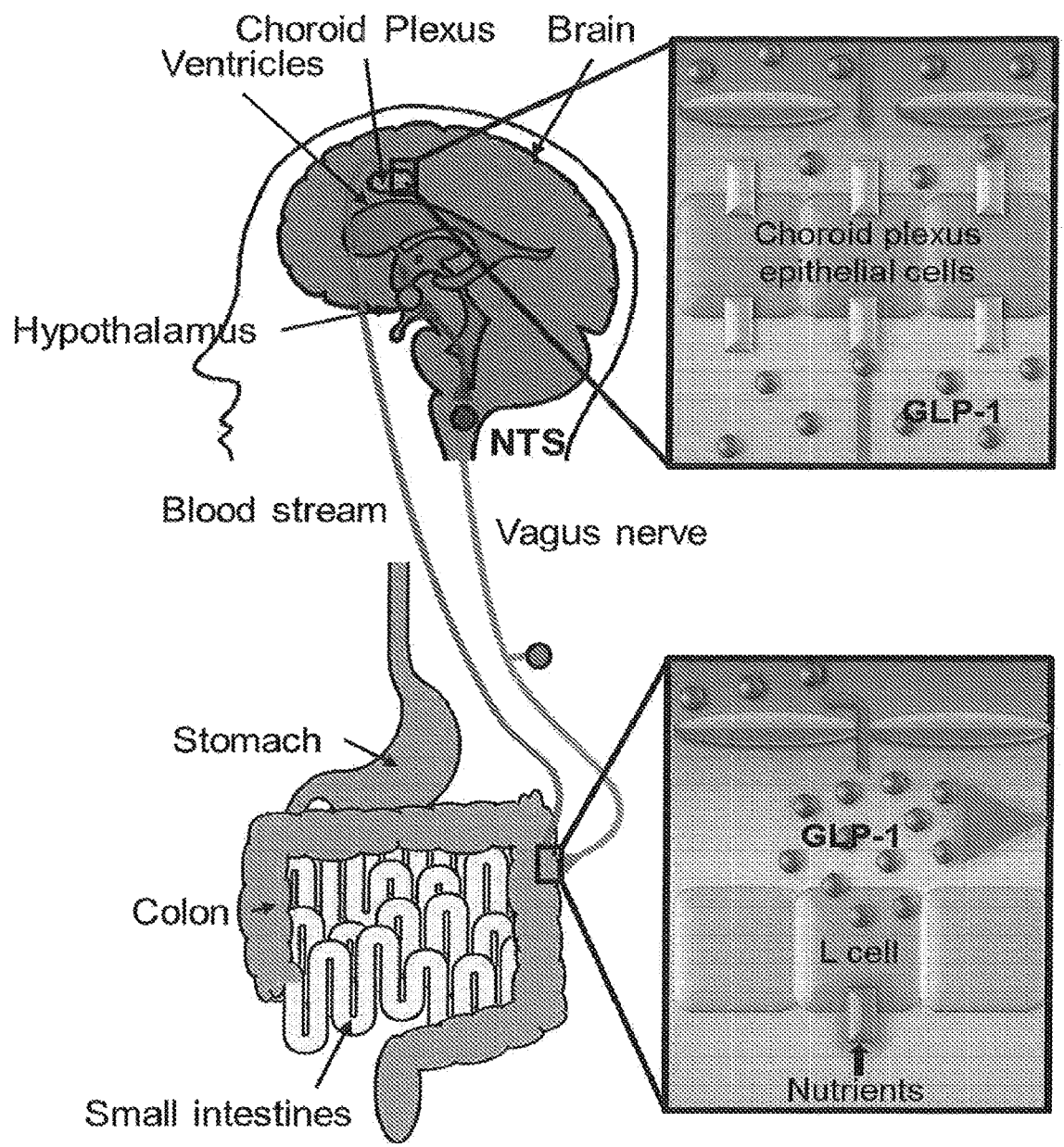

Gabrielian, L. et al., "Intracranial Pressure Changes following Traumatic Brain Injury in Rats: Lack of Significant Change in the Absence of Mass Lesions or Hypoxia", Journal of Neurotrauma, vol. 28, 2011, pp. 2103-2111.
Mollan, S.P. et al., "Idiopathic intracranial hypertension: consensus guidelines on management", www.jnnp.com, vol. 89, 2018, pp. 1088-1100.
Markey, K.A. et al., "Understanding idiopathic intracranial hypertension: mechanism, management, and future directions", www.thelancet.com/neurology, vol. 15, 2016, pp. 78-91.
Lindgren, S. et al., "Experimental Studies in Head Injury", Biophysik, vol. 3, 1966, pp. 174-180.
Mollan, S.P. et al., "The expanding burden of idiopathic intracranial hypertension", Springer Nature, 2018, pp. 1-8.
Murtha, L.A. et al., "Intracranial pressure elevation after ischemic stroke in rats: cerebral edema is not the only cause, and short-duration mild hypothermia is a highly effective preventive therapy", Journal of Cerebral Blood Flow & Metabolism, vol. 35, 2015, pp. 592-600.
O'Reilly, M.W. et al., "A unique androgen excess signature in idiopathic intracranial hypertension is linked to cerebrospinal fluid dynamics", Research article, 2019, pp. 1-10.
Pedersen, S. H. et al., "The Relationship Between Intracranial Pressure and Age-Chasing Age-Related Reference Values", Original article, 2017, pahes:1-5.
Eftekhari, S. et al., "Preclinical update on regulation of intracranial pressure in relation to idiopathic intracranial hypertension", Fluids and Barriers of the CNS, 2019, pp. 1-12.
Sorby-Adams, A.J. et al., "Determining the Temporal Profile of Intracranial Pressure Changes Following Transient Stroke in an Ovine Model", Frontiers in Neuroscience, Original Research, vol. 13, Article 587, 2019, pp. 1-16.
Eakin, Katharine, "Exendin-4 Ameliorates Traumatic Brain Injury-Induced. Cognitive Impairment in Rats", PLOS ONE | www.plosone.org, 2013, vol. 8, Issue 12, e82016; pp. 1-8.
Dixon, Edward C., "A fluid percussion model of experimental brain injury in the rat", J. Neurosurg., vol. 67, 1987, pp. 110-119.
HHS, U.S. Department of Health and Human Services Food and Drug Administration Center for Drug Evaluation and Research (CDER), 2005, Pharmacology and Toxicology.
Neumiller, J.J., "Pharmacology, efficacy and safety of liraglutide in the management of type 2 diabetes", Diabetes, Metabolic Syndrome and Obesity: Targets and Therapy, 2010, vol. 3, pp. 2015-2226.
Web MD (Cerebral Edema (Brain Swelling), accessed on May 2, 2019, see p. 4).
Prins, M.L., "Fluid percussion brain injury in the developing and adult rat: a comparative study of mortality, morphology, intracranial pressure and mean arterial blood pressure", Developmental Brain Research, vol. 95, 1996, pp. 272-282.
Botfield, H., et al., "GLP-1 reduces cerebrospinal fluid secretion and intracranial pressure: a novel treatment for idiopathic intracranial hypertension?" Endocrine Abstracts, vol. 38, 2015.
Forster, N., et al., "Managing elevated intracranial pressure", Current Opinion in Anesthesiology, vol. 17, No. 5, 2004, pp. 371-376.
Hakon, J., et al., "Preservation of the Blood Brain Barrier and Cortical Neuronal Tissue by Liraglutide, a Long Acting Glucagon-Like-1 Analogue, after Experimental Traumatic Brain Injury", PLOS one, 2015, vol. 10, No. 3, e0120074; pp. 1-17.
Hou, J. et al., "Liraglutide, a long-acting GLP-1 mimetic, and its metabolite attenuate inflammation after intracerebral hemorrhage", Journal of Cerebral Blood Flow & Metabolism, vol. 32, No. 12, 2012, pp. 2201-2210.
Meier, J., "GLP-1 receptor agonists for individualized treatment of type 2 diabetes mellitus", Nature Reviews Endocrinology, vol. 8, 2012, pp. 728-742.
Neumiller, J., "Differential chemistry (structure), mechanism of action, and pharmacology of GLP-1 receptor agonists and DPP-4inhibitors", Journal of American Pharmacists Association, vol. 49, No. 5, 2009, pp. S16-S29.
Tweedie, D., et al., "Exendin-4, a glucagon-like peptide-1 receptor agonist prevents mTBI-induced changes in hippocampus gene expression and memory deficits in mice", Experimental Neurology, vol. 239, 2013, pp. 170-182.
International Search Report and Written Opinion dated Dec. 7, 2015 for corresponding PCT Application No. PCT/GB2015/052453.
International Preliminary Report on Patentability dated Mar. 7, 2017 for corresponding PCT Application No. PCT/GB2015/052453.
David Parkes et al., "Pharmacokinetic Actions of Exendin-4 in the Rat: Comparison With Glucagon-Like Peptide-1," Research Article, Drug Development Research, vol. 35, 2001, pp. 260-267.
Christakis et al., "Abstract," J. Invest Surg., 2017, pp. 162-169.

* cited by examiner

ELEVATED INTRACRANIAL PRESSURE TREATMENT

CROSS-REFERENCE TO RELATED APPLICATIONS

This application claims priority to and is a continuation of U.S. patent application Ser. No. 15/504,399, filed on Feb. 16, 2017, which is a national stage application (under 35 U.S.C. § 371) of PCT/GB2015/052453, filed Aug. 25, 2015, which claims benefit of United Kingdom Application No. 1415598.0, filed Sep. 3, 2014, which are incorporated herein by reference in their entireties.

FIELD OF THE INVENTION

The present invention relates to the treatment of undesirable increased intra-cranial pressure which may be due to irregularities in cerebral spinal fluid (CSF) secretion within/ from the brain. Increased intracranial pressure is observed, for example, in subjects with idiopathic intracranial hypertension (IIH), secondary pseudotumour cerebri, hydrocephalus, normal pressure hydrocephalus, raised intracranial pressure secondary to a brain tumour, meningitis, brain trauma, brain injury, and venous sinus thrombosis.

BACKGROUND TO THE INVENTION

Elevated intracranial pressure (ICP) can be due to a rise in pressure of the cerebrospinal fluid (CSF), the fluid which surrounds the brain and spinal cord. An increase in ICP is a serious medical condition, as the increased pressure can lead to damage of the brain or spinal cord by pressing on important brain structures and by restricting blood flow into the brain. Thus, effective treatments to alleviate elevated ICP are required.

One condition associated with elevated ICP is IIH, also known as benign intracranial hypertension or pseudotumour cerebri, which is a condition of unknown aetiology characterised by elevated ICP and papilloedema. IIH is a condition found in obese women (90% of incidences), causing disabling daily headaches and visual loss, which is severe and permanent in up to 25% of cases (1). Effective treatments are lacking and range from unproven medical therapy to surgical procedures with associated morbidity and poor long term efficacy (8). Amongst the obese female population the incidence of IIH is 20 per 100,000. Worldwide, the number of obese individuals has doubled since 1980 with 22.7% of the UK population being characterised as obese (body mass index (BMI) >30 kg/m$^2$) (2) and in line with the global epidemic of obesity the prevalence of IIH is expected to rise and consequently contribute significant morbidity to the young female obese population.

Although the aetiology of IIH is not known it is thought to relate to disordered CSF dynamics, with either enhanced CSF production at the choroid plexus (CP) and/or restricted CSF drainage at the arachnoid granulation tissue (AGT)(3).

The 2005 Cochrane review concluded that there was insufficient evidence to determine which treatments were potentially beneficial and which were harmful in IIH (4); hence there are no specific guidelines regarding the treatment of IIH. Typically however, carbonic anhydrase inhibitors have been used with the aim of lowering ICP, although evidence of efficacy is lacking (5). Topiramate, a carbonic anhydrase inhibitor with weight loss properties, has been evaluated in IIH and was found to induce weight loss but this trial is difficult to interpret since no therapeutic benefit on IIH was noted above the control cohort treated with Acetazolamide (visual field grades improved from baseline in both groups, but there was no statistically significant difference between groups) (6).

In cases of deteriorating vision, surgical techniques such as cerebrospinal fluid (CSF) diversion (shunting) or optic nerve sheath fenestration are used to prevent blindness (7). The incidence of CSF shunting procedures to lower ICP is rising rapidly in the USA in line with the growing obesity FIG. 7). However, shunting itself is a far from satisfactory treatment of IIH and is of course very invasive. Patients waiting for a shunt and suffering disabling headaches with very high pressures can also be offered repeated lumbar punctures to lower ICP and thereby offer symptomatic relief.

It is amongst the objects of the present invention to provide a method of reducing elevated ICP such as observed with patients suffering from IIH. It is also amongst the objects of the present invention to obviate and/or mitigate at least one of the aforementioned disadvantages.

SUMMARY OF THE INVENTION

In a first aspect, there is provided an incretin, such as GLP-1 or analogue or derivative thereof, an incretin receptor agonist or an incretin enhancer, such as a DPP IV inhibitor or variants and combinations thereof, for use in a method of reducing elevated intracranial pressure (ICP) in a subject.

In a further aspect there is provided a method of reducing elevated ICP in a subject suffering from elevated ICP, the method comprising administering an incretin, such as GLP-1 or analogue or derivative thereof, an incretin receptor agonist or an incretin enhancer, such as a DPP IV inhibitor, or variants and combinations thereof, in an amount sufficient to cause a reduction in elevated ICP in the subject.

The elevated ICP may be associated with, for example, idiopathic intracranial hypertension (IIH), secondary pseudotumour cerebri, hydrocephalus, normal pressure hydrocephalus, raised intracranial pressure secondary to a brain tumour, meningitis, brain trauma, brain injury, and venous sinus thrombosis. Thus the incretin, such as GLP-1 or analogue thereof, the incretin receptor agonist or the incretin enhancer, such as a DPP IV inhibitor, may be used in a method of preventing or treating one or more of the aforementioned conditions. In certain embodiments the present invention may exclude treatment of one or more of the conditions identified above.

Without wishing to be bound by theory, it is hypothesised that activation of the GLP-1 receptor in epithelial cells of the choroid plexus may lead to the conversion of ATP to cAMP, which in turn leads to activation of protein kinase A (PKA) which phosphorylates the Na$^+$H$^+$ exchanger resulting in its inhibition. A reduction in Na+ transport from the blood into the CSF is expected to result in a reduction in water movement and hence CSF production.

Thus, in accordance with the present invention, the incretin, such as GLP-1 or analogue thereof, an incretin receptor agonist or an incretin enhancer, such as a DPP IV inhibitor or combinations thereof of the present invention may be intended to act on GLP-1 receptors found in epithelial cells of the choroid plexus.

As used herein, the term "GLP-1" is to be understood to include a naturally occurring glucagon-like peptide-1 (GLP-1) polypeptide and/or naturally occurring or artificial variants or analogues of GLP-1, including but not limited to GLP-1 (7-36) amide and GLP-1 (7-37). Natural GLP-1 has a relatively short-half life in plasma, as it is susceptible to enzymic degradation by the DPP IV enzyme. Thus, a number of GLP-1 analogues are designed to have a longer half-life and/or be resistant to DDP IV degradation. Exemplary, non-limiting examples of such GLP-1 polypeptides are described for example in U.S. Patent Publication No. 2008/0015144 and U.S. Patent Publication No. 2011/0274747, herein incorporated by reference in their entireties.

Specific Examples of GLP-1 Analogues Include Albglutide (Marketed by GSK) and Liraglutide (Marketed by Novo Nordisk)

Incretin, such as GLP-1, receptor agonists include mimetics of the incretins which are designed to act in a similar manner to the incretin itself. Examples of GLP-1 mimetics include exendins and analogues thereof. Exendin-3, for example is present in the salivary secretions of *Heloderma horridum* (Mexican Beaded Lizard), and exendin-4 is present in the salivary secretions of *Heloderm suspectum* (Gila monster) (Eng, J., et al., J. Biol. Chem., 265:20259-62, 1990; Eng, J., et al., J. Biol. Chem., 267:7402-05, 1992). As well as the natural exendins, analogues thereof are known and may find application in the present invention. Exendin analogues are described, for example in WO 99/07404, WO 99/25727, WO 99/25728, WO 99/40788, WO 00/41546, WO 00/41548, WO09035540 herein incorporated by reference in their entireties.

The term "agonist", as used herein, shall mean an agent (e.g., ligand, or compound) that by virtue of binding to an incretin receptor, such as GLP-1 receptor, activates the receptor so as to elicit an intracellular response mediated by the receptor.

By "exendin agonist" is meant a compound which mimics the effects of an exendins, e.g. on gastric motility and gastric emptying (namely, a compound which effectively binds to the receptor at which exendins exert their action on gastric motility and gastric emptying, preferably an analog or derivative of an exendin) or a compound, e.g. that mimics the effects of exendin on the reduction of food intake by binding to the receptor or receptors where exendin causes this effect.

A specific example of an exendin molecule is Exenatide which is currently marketed by Amylin Pharmaceuticals, Inc. and Eli Lilly and Company.

A "derivative" includes any base molecule or analog having a chemical modification within, attached or linked to, or associated with the molecule. Such chemical modifications can include internal linkers (e.g., spacing or structure-inducing) or appended molecules, such as molecular weight-enhancing molecules (e.g., polyethylene glycol (PEG)), or tissue targeting molecules. Examples of such molecules are known in the art, for example, insulinotropic peptides, including GLP-1 and exendin, modified with a maleimide group are described in U.S. Pat. No. 6,593,295, incorporated herein by reference.

A "variant" includes any modification to the base molecule, analog or variant not encompassed in the terms "analog" and "derivative," as would be known to a person of ordinary skill in the art. For example, variants may include proforms or chimeras of a selected molecule. Small molecules are included in the compounds useful in the invention to the extent that they bind to a receptor for GLP-1 or exendin. Not all of the peptide molecules described as incretins, glucagon-like peptide-1 (GLP-1), exendins, or analogs, derivatives, or variants may bind to a receptor for GLP-1, although they are still useful in the invention by virtue of a pharmacology not dependent on a known GLP-1 receptor. These molecules may still possess the desired biological activities described herein. Other compounds encompassed within the scope of the invention include those described in U.S. Pat. Nos. 6,569,832; 6,528,486; 6,514,500; 6,458,924; 6,451,987; 6,451,974; 6,268,343, all herein incorporated by reference.

In certain embodiments of the present invention, for the avoidance of doubt the GLP-1 analogue or agonist is not a bombesin-like receptor 3 (BRS-3) agonist, as described for example in WO07027225.

As mentioned above natural GLP-1 is susceptible to degradation by the enzyme DDP IV. Thus another way to enhance the effectiveness of GLP-1 is to administer a DDP IV inhibitor.

The term "DPP-IV inhibitor," as used herein, refers to a compound that binds to DPP-IV and inhibits DPP-IV dipeptidyl peptidase activity. The term "selective DPP-IV inhibitor," as used herein, refers to a DPP-IV inhibitor having selectivity for DPP-PV over closely related peptidases, such as one or more of post-proline-cleaving enzyme (PPCE), dipeptidyl peptidase II (DPP-II), dipeptidyl peptidase 8 (DPP-8), and dipeptidyl peptidase 9 (DPP-9).

Examples of DPP-IV inhibitors are described in Villhauer et al., J Med Chem (2003) 46:2774-2789, for LAF237; Ahren et al, J Clin Endocrinol Metab (2004) 89:2078-2084; Villhauer et al., J Med Chem (2002) 45:2362-2365 for NVP-DPP728; Ahren et al, Diabetes Care (2002) 25:869-875 for NVP-DPP728; Peters et al., Bioorg Med Chem Lett (2004) 14:1491-1493; Caldwell et al., Bioorg Med Chem Lett (2004) 14:1265-1268; Edmondson et al., Bioorg Med Chem Lett (2004) 14:5151-5155; and Abe et al., J Nat Prod (2004) 67:999-1004; the disclosure of each of which is herein incorporated by reference in its entirety. Specific examples of DPP-IV inhibitors include, but are not limited to, dipeptide derivatives or dipeptide mimetics such as alanine-pyrrolidide, isoleucine-thiazolidide, and the pseudo-substrate N-valyl prolyl, 0-benzoyl hydroxylamine, as described e.g. in U.S. Pat. No. 6,303,661, the disclosure of which is herein incorporated by reference in its entirety. Examples of DPP-IV inhibitors may be found in U.S. Pat. Nos. 6,812,350, 6,803,357, 6,710,040, 6,617,340, 6,699,871, 6,573,287, 6,432,969, 6,395,767, 6,303,661, 6,242,422, 6,166,063, the disclosure of each of which is herein incorporated by reference in its entirety.

Further examples of DPP-IV inhibitors may be found in International Applications WO 04/103993, WO 04/103276, WO 04/99134, WO 04/87053, WO 04/76434, WO 04/76433, WO 04/69162, WO 04/64778, WO 04/71454, WO 04/69162, WO 04/67509, WO 04/58266, WO 04/52850, WO 04/50022, WO 04/50658, WO 04/32836, WO 04/46106, WO 04/43940, WO 04/41795, WO 04/37169, WO 04/37181, WO 03/101958, WO 04/14860, WO 04/07468, WO 04/04661, WO 03/82817, WO 03/72528, WO 03/57666, WO 03/57144, WO 03/40174, WO 03/37327, WO 03/35067, WO 03/35057, WO03/22871, WO 03/15775, WO 03/04498, WO 03/02530, WO 03/02596, WO 03/02595, WO 03/02593, WO 03/02553, WO 03/02531, WO 03/00181, WO 03/00180, WO 03/00250, WO 02/83109, WO 02/83128, WO 02/76450, WO 02/51836, WO 02/34900, WO 01/96295, WO 01/81337, WO 01/81304, WO 01/68603 WO 01/34594, WO 00/34241, WO 00/23421, WO 99/67278, WO 99/61431, WO 98/19998, WO 97/40832 each of which is herein incorporated by reference in its entirety.

Examples of specific DDP IV inhibitors which may be of use in the present invention include vildagliptin, saxagliptin, azetidine, sitagliptin, omarigliptin, alogliptin, and linagliptin.

The agents described herein may be administered alone or in combination. Moreover, they may also be used in combination with other pharmaceutical agents. The agents themselves or combinations of agents may be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s). Moreover it should be appreciated that in a combination therapy, each component need not be administered in the same manner. For example one therapy may be administered by injection and another therapy by oral administration.

The compounds of the invention may also be administered in conjunction with non-chemical treatments such as radiotherapy, photodynamic therapy, gene therapy; surgery and/or controlled diets.

The subject is typically an animal, e.g. a mammal, especially a human. In one embodiment the subject is not considered to be clinically obese and/or being treated for diabetes.

By a therapeutically or prophylactically effective amount is meant one capable of achieving the desired response, and will be adjudged, typically, by a medical practitioner. The amount required will depend upon one or more of at least the active compound(s) concerned, the patient, the condition it is desired to treat or prevent and the formulation of order of from 1 µg to 1 g of compound per kg of body weight of the patient being treated.

In some embodiments, the incretin, or analogue thereof, the incretin receptor agonist or the incretin enhancer is administered at a dose of at least 1, at least 2, at least 3 or at least 5 µg of compound per kg of body weight of the subject being treated. The dose may be less than 20, less than 15 or less than 10 µg/kg. In some embodiments, the dose is from 1 to 10, from 2 to 8 or from 3 to 6 µg/kg, for example 5 µg/kg.

In some embodiments, an incretin receptor agonist, such as an exendin (e.g. exendin-4), is administered at a dose of from 1 to 10, from 2 to 8 or from 3 to 6 µg/kg, for example 5 µg/kg.

Different dosing regimens may likewise be administered, again typically at the discretion of the medical practitioner. The agents may be administered by at least daily administration although regimes where the agent(s) is (or are) administered more infrequently, e.g. every other day, weekly or fortnightly, for example, are also embraced by the present invention.

By treatment is meant herein at least an amelioration of a condition suffered by a patient; the treatment need not be curative (i.e. resulting in obviation of the condition). Analogously references herein to prevention or prophylaxis herein do not indicate or require complete prevention of a condition; its manifestation may instead be reduced or delayed via prophylaxis or prevention according to the present invention.

For use according to the present invention, the compounds or physiologically acceptable salt, solvate, ester or other physiologically acceptable functional derivative thereof described herein may be presented as a pharmaceutical formulation, comprising the compound or physiologically acceptable salt, ester or other physiologically functional derivative thereof, together with one or more pharmaceutically acceptable carriers therefor and optionally other therapeutic and/or prophylactic ingredients. Any carrier(s) are acceptable in the sense of being compatible with the other ingredients of the formulation and not deleterious to the recipient thereof.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Physiologically functional derivatives of compounds of the present invention are derivatives, which can be converted in the body into the parent compound. Such physiologically functional derivatives may also be referred to as "pro-drugs" or "bioprecursors". Physiologically functional derivatives of compounds of the present invention include hydrolysable esters or amides, particularly esters, in vivo. Determination of suitable physiologically acceptable esters and amides is well within the skills of those skilled in the art. Derivatives may also include modification of an agent to include a group, such as a PEG or other group which may have a desirable physiological effect on the agent.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a monohydrate, di-hydrate, tri-hydrate etc, depending on the number of water molecules present per molecule of substrate.

It will be appreciated that the agents of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I) or (II) as well as wholly or partially racemic mixtures of such enantiomers.

The compounds of the present invention may be prepared using reagents and techniques readily available in the art.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. Nasal and/or buccal administration may be particularly preferred in certain embodiments. The formulation may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use. Particularly preferred route of injectable administration in certain embodiments may include intra-arterial, such as via the carotid and/or ventral arteries, or intraventricular and/or intrathecal administration to the brain ventricles or via a lumbar puncture. Administration close to site of action or to fluid which is carried to the brain may be advantageous. It may be possible to use incretins, such as GLP-1 even when they are susceptible to degradation by DPP IV enzymes in such situations. In certain embodiments of the present invention it may be desirable for the treatments envisaged by the present invention to substantially treat elevated ICP and not to have an effect outside the brain.

An active compound may also be formulated as long-acting depot preparations, which may be administered by intramuscular injection or by implantation, e.g., subcutaneously or intramuscularly, or in the gut for example Depot preparations may include, for example, suitable polymeric or hydrophobic materials, or ion-exchange resins. Such long-acting formulations are particularly convenient for prophylactic and/or prolonged administration.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microlitres, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension. Of particular relevance to the present invention is the ability of an intranasal delivered GLP-1 agonist to reach the brain and CSF in high concentrations (20),(37). Thus is certain preferred embodiments of the present invention, the agent(s) of the invention may be administered nasally.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied directly or carried on a suitable support such as a bandage, gauze, mesh or the like which may be applied to and over the area to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

DETAILED DESCRIPTION

Figure 2:
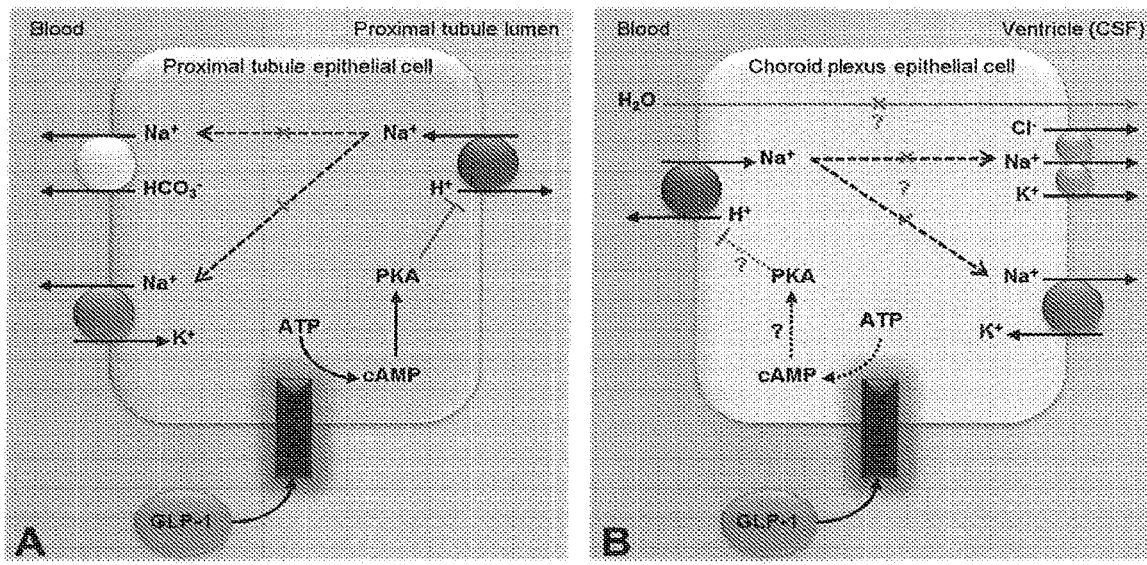
Figure 3:
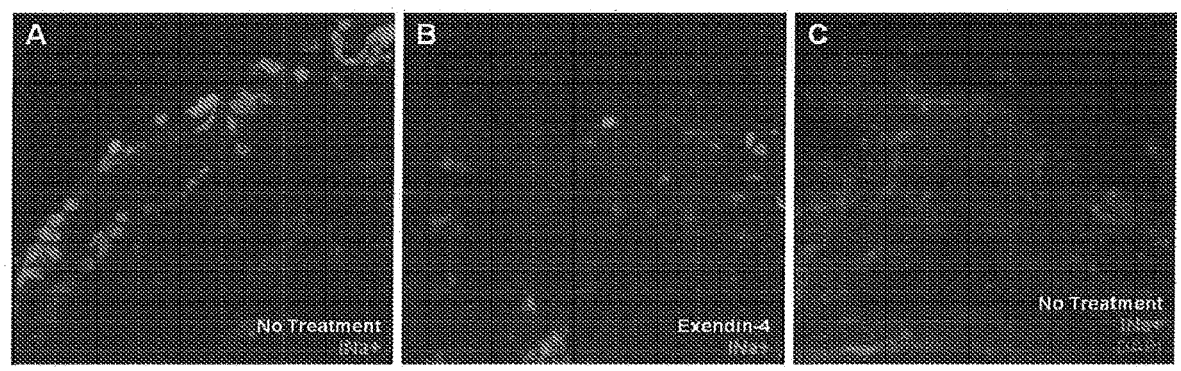
Figure 4:
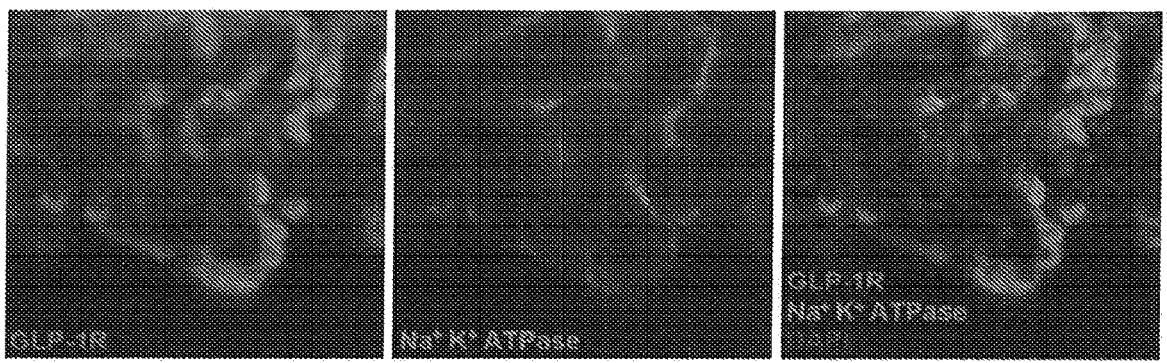
Figure 5:
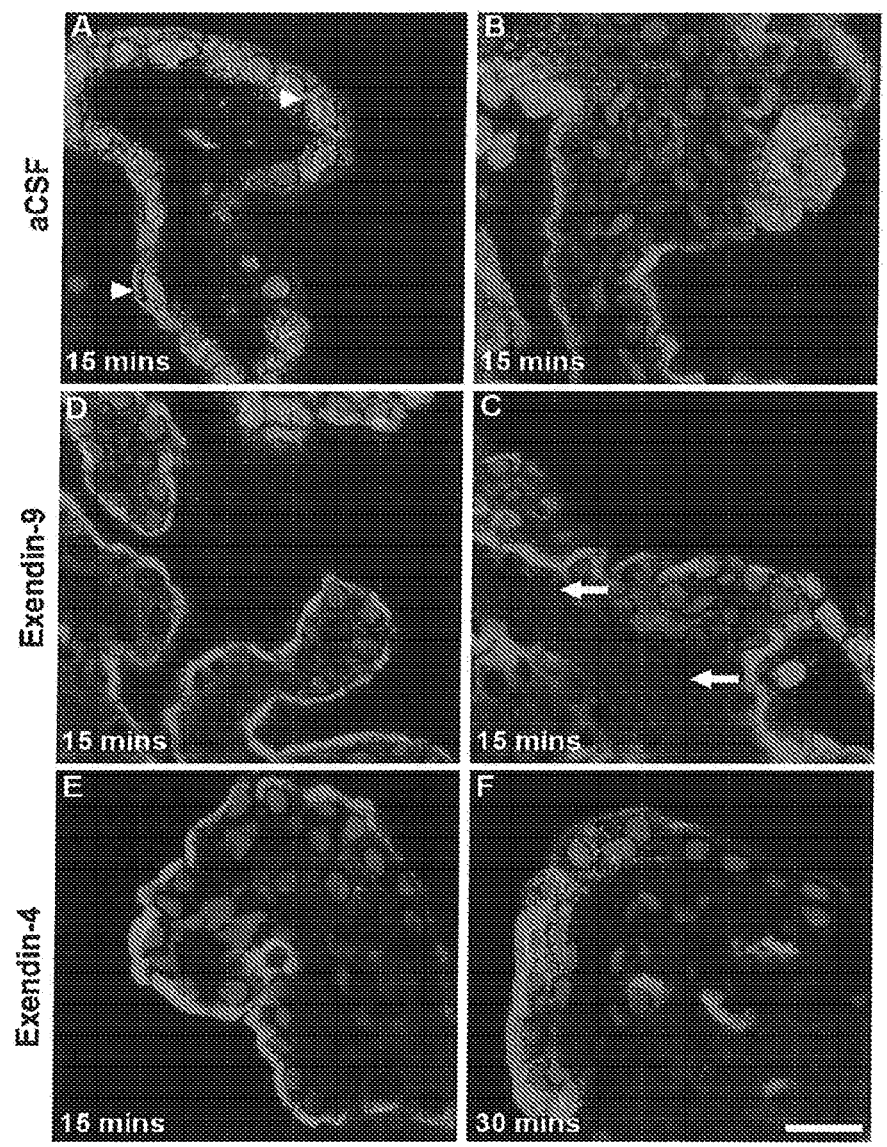
Figure 6:
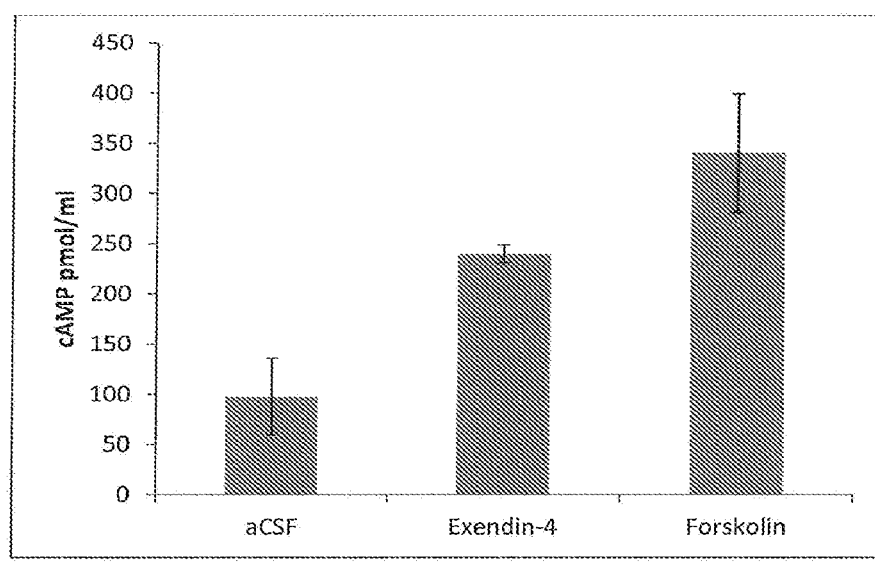
Figure 7:
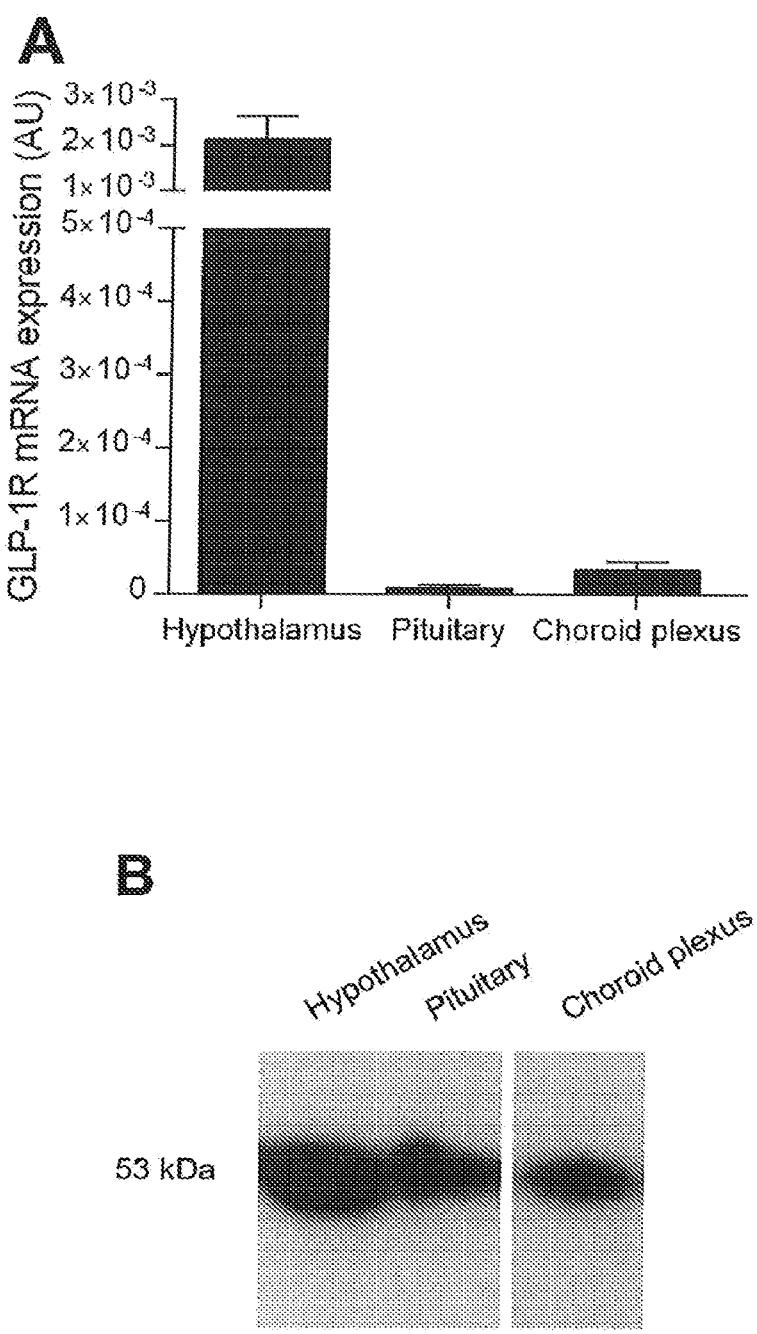
Figure 8:
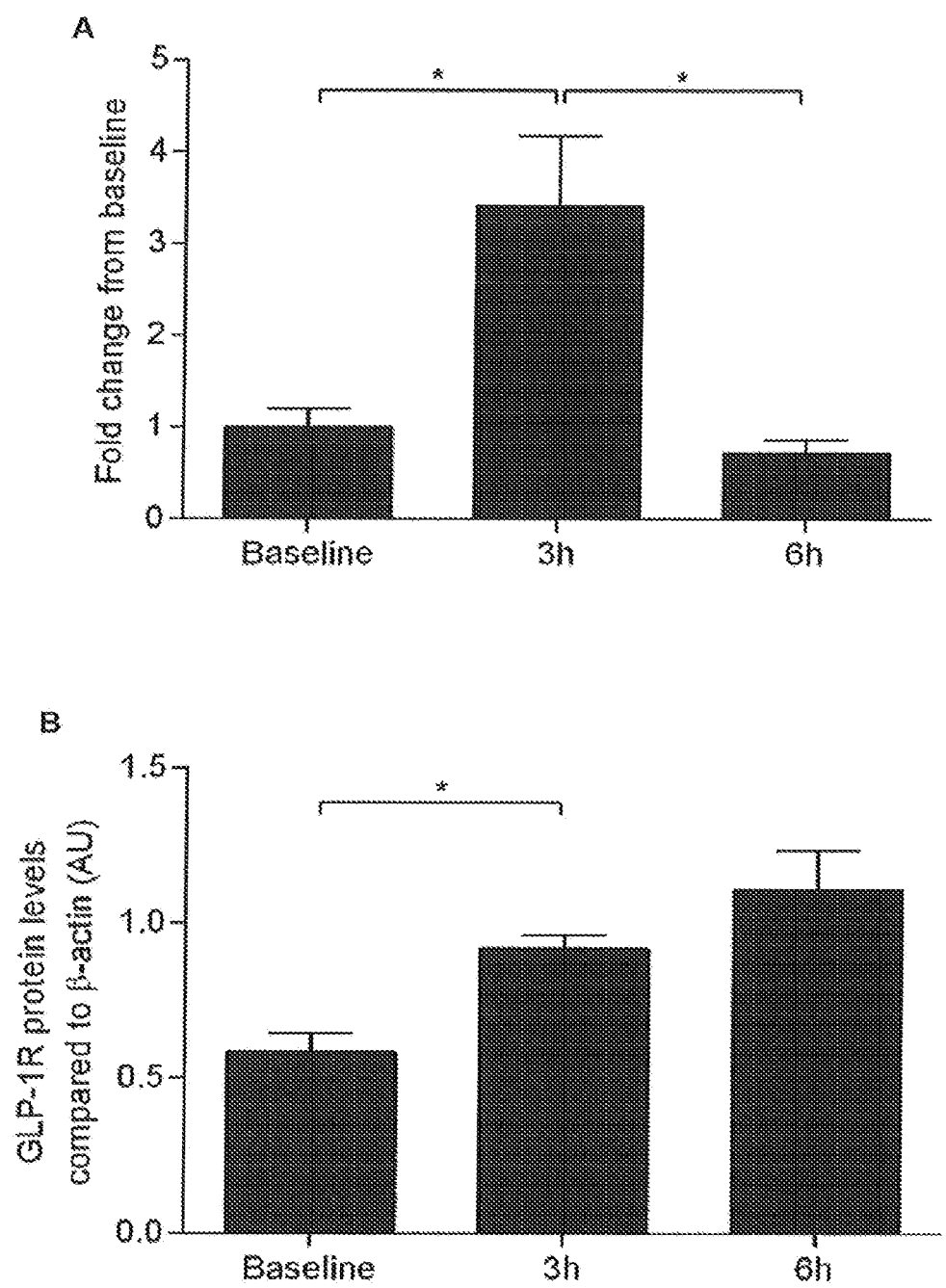

The present invention will now be further described by way of example and with reference to the figures which show:

FIG. 1 is a diagram representing the possible routes for GLP-1 from the gut to the choroid plexus. GLP-1 is secreted by L cells in response to nutrients in the gut. GLP-1 diffuses across the basal lamina and either enters the capillaries or activates the vagus nerve. Once in the bloodstream, GLP-1 could be transported directly to the choroid plexus where it would bind to GLP-1 receptors on the basal surface of the choroid plexus epithelial cells. Alternatively the signal may be transmitted via the vagus nerve which synapses with the nucleus of the solitary tract (NTS). Neurones in the NST also produce GLP-1 and their fibres project to areas of the brain, including the hypothalamus, which are in contact with ventricle and CSF. Therefore GLP-1 may be secreted into the CSF allowing it to bind with GLP-1 receptors on the apical surface of the choroid plexus epithelial cells. En cell—endothelial cell, CPe cell—choroid plexus epithelial cell;

FIG. 2 is a diagrammatical representation of GLP-1 influence on fluid homeostasis. (A) In the proximal tubule of the kidney, the binding of GLP-1 to the GLP-1R stimulates the conversion of ATP to cAMP by adenylate cyclase. cAMP activates protein kinase A (PKA) which phosphorylates the $Na^+H^+$ exchanger resulting in its inhibition. This prevents $Na^+$ reabsorption from the proximal tubule lumen into the bloodstream. (B) It is hypothesised that GLP-1 has a similar effect in the choroid plexus as GLP-1R are present on the choroid plexus epithelial cells. A reduction in $Na^+$ transport from the blood into the CSF would result in a reduction in water movement and CSF production;

FIG. 3 shows the Effects of Exendin-4 on intracellular $Na^+$ levels in rat choroid plexus explants. Intracellular $Na^+$ levels were observed using Sodium Green ($iNa^+$) (life technologies). Briefly, rat choroid plexus explants were incubated with $iNa^+$ for 30 minutes before treatment with artificial CSF (no treatment) or artificial CSF+Exendin-4 for 3 hours. The fluorescence intensity directly correlates with the amount of intracellular $Na^+$. There were higher numbers of intense fluorescent choroid plexus epithelial cells with no treatment (A) compared to treatment with Exendin-4 (B). This suggests that $Na^+$ transport into the cell was reduced, possibly through Exendin-4 mediated inhibition of the Na+/H+ exchanger. (C) Counterstaining with DAPI, a nuclear marker, demonstrates the $N^+$ is intracellular;

FIG. 4 shows GLP-1 receptor and $NA^+K^+ATPase$ staining in the choroid plexus. Representative image of GLP-1R (red—left image) and $Na^+K^+ATPase$ (green—middle image) in the choroid plexus. GLP-1R staining was observed in the cytoplasm of the choroid plexus epithelial cells. GLP-1R was also present on the apical surface as indicated by co-localisation with $Na^+K^+ATPase$—right hand image. DAPI (blue) was used as a generic nuclear marker;

FIG. 5 shows the effects of GLP-1 receptor localisation after stimulation with a GLP-1 agonist. Representative images of GLP-1R staining (green) in choroid plexus explants treated with artificial CSF (aCSF), Exendin-4 (GLP-1R agonist), and Exendin-9 (GLP-1R antagonist) for the time periods indicated. In aCSF (A,B) GLP-1R staining was observed throughout the choroid plexus epithelial cell cytoplasm, with a higher intensity of staining on the apical surface and in the junction between cells (white arrowhead). With the addition of Exendin-9 (C) the GLP-1R positive staining was restricted to the apical membrane after 15 minutes. (D) The GLP-1R positive staining did not appear to be localised to the basal membrane of the choroid plexus epithelial cells or in endothelial cells (white arrows). (E) Fifteen minutes of Exendin-4 treatment also caused relocation of the GLP-1R to the apical surface of the choroid plexus epithelial cells. However, by 30 minutes the receptor became internalised (F). DAPI (blue) was used as a generic nuclear marker, scale bar—20 µm;

FIG. 6 shows a graph displaying cAMP levels in choroid plexus tissue after stimulation with a GLP-1 agonist and other agents. Histogram of mean±SEM of cAMP levels in choroid plexus explants in the 3 groups. The normal levels of cAMP observed with aCSF were increased after the addition of Exendin-4 (GLP-1R agonist) for 3 hours. Forskolin, an adenylate cyclase activator, acted as a positive control for cAMP levels;

FIG. 7 shows the expression of GLP-1R mRNA and protein in the rat hypothalamus, pituitary gland, liver and choroid plexus. (A) The levels of GLP-1R mRNA were determined by QPCR and compared against a reference gene (18S). The histogram represents the mean±SEM of GLP-1R mRNA expression (arbitrary units). High levels of GLP-1R mRNA were detected in the hypothalamus where GLP-1 has the majority of its action, and the pituitary showed minimal GLP-1R mRNA expression. GLP-1R mRNA was also detected in the choroid plexus. (B) Western Blot analysis of GLP-1R protein levels showing a single band observed at 53 kDa. High GLP-1R protein levels were observed in the hypothalamus and lower levels in the pituitary gland and choroid plexus. These studies demonstrate that the choroid plexus express GLP-1R mRNA and protein;

FIG. 8 shows the change in GLP-1R expression after agonist stimulation in rat choroid explants. (A) The histogram represents the mean±SEM of the fold change in GLP-1R mRNA from baseline. The levels of GLP-1R mRNA increased in the choroid plexus explants after 3 hours of treatment and then returned to basal levels by 6 hours. (B)

The histogram represents the mean±SEM of the GLP-1R protein levels compared to β-actin (arbitrary units). GLP-1R protein levels were also raised at 3 and 6 hours.

Figure 9:
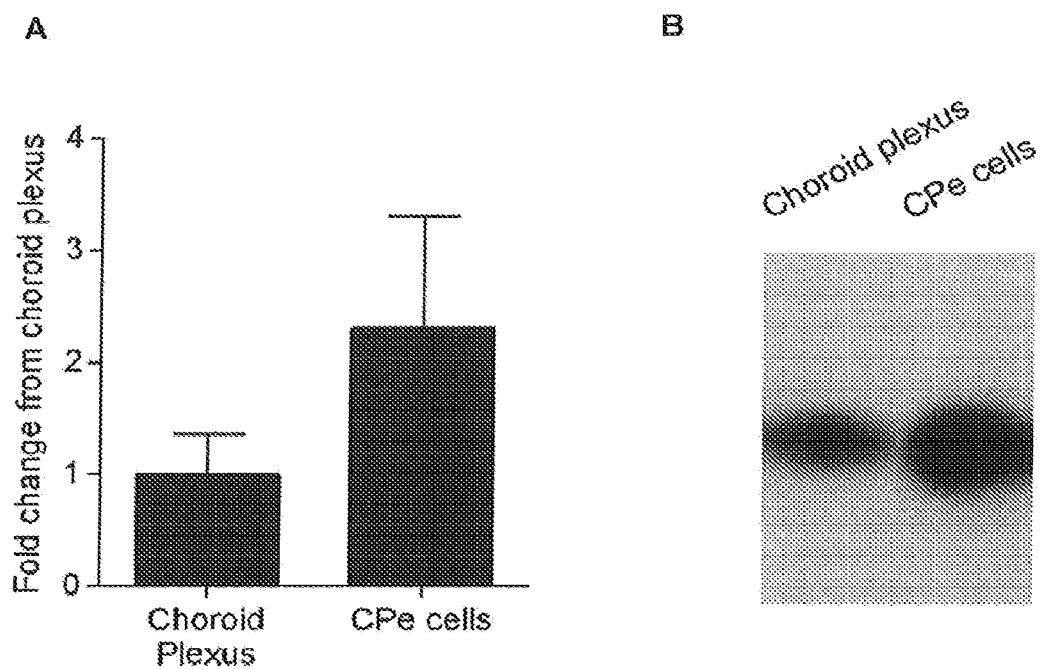
Figure 10:
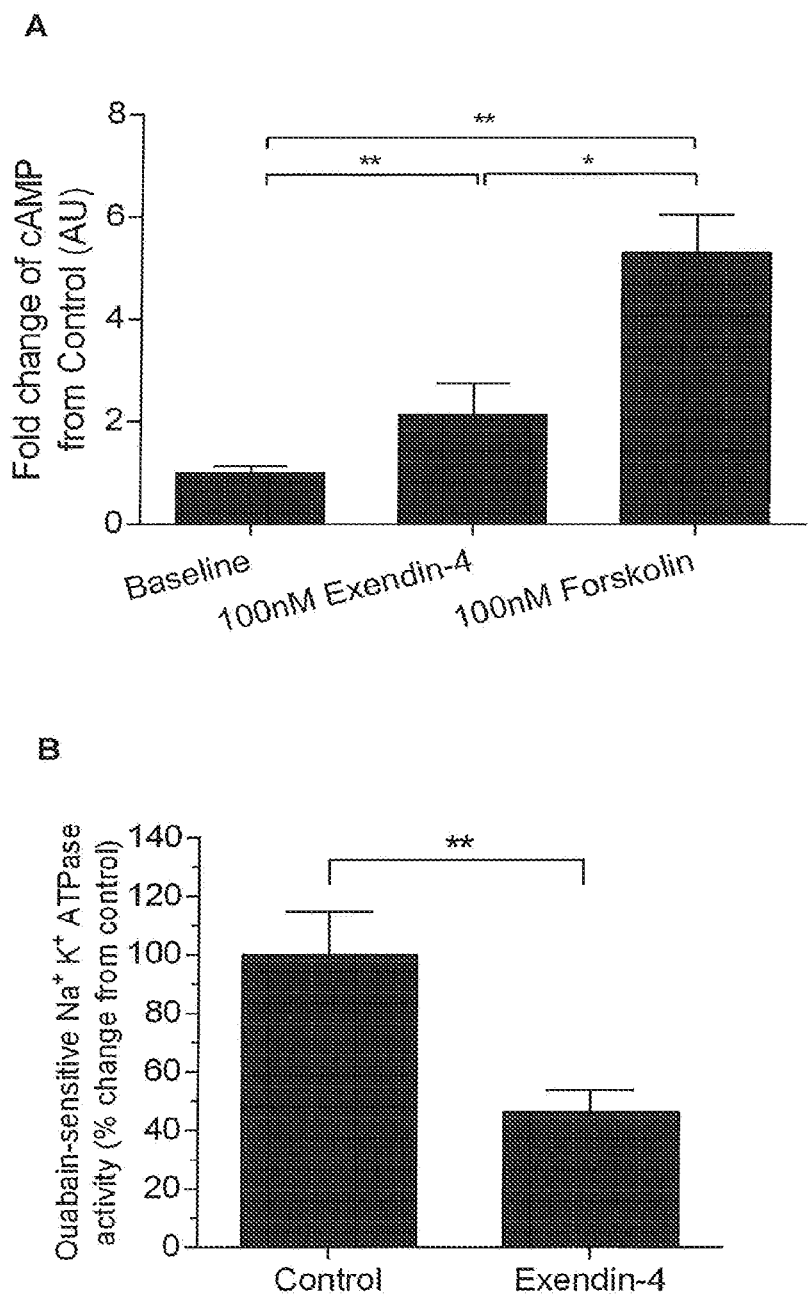
Figure 11:
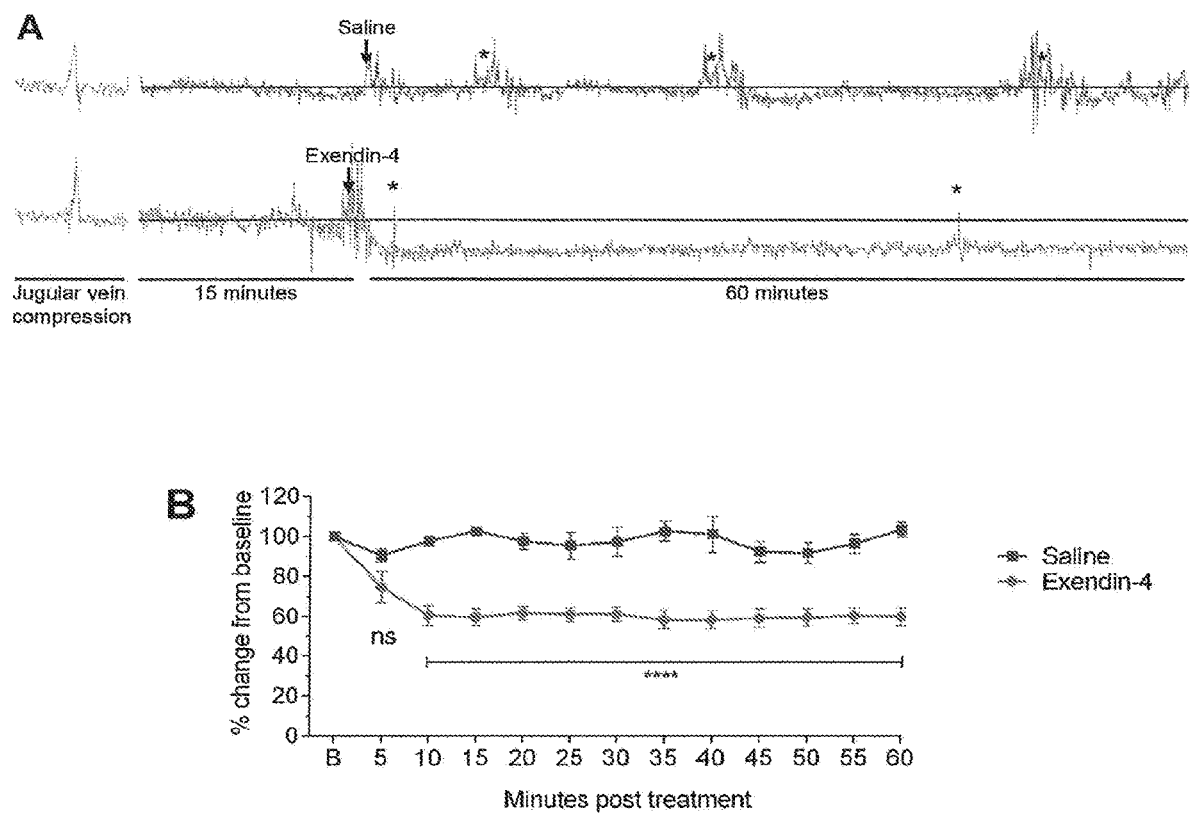
Figure 12:
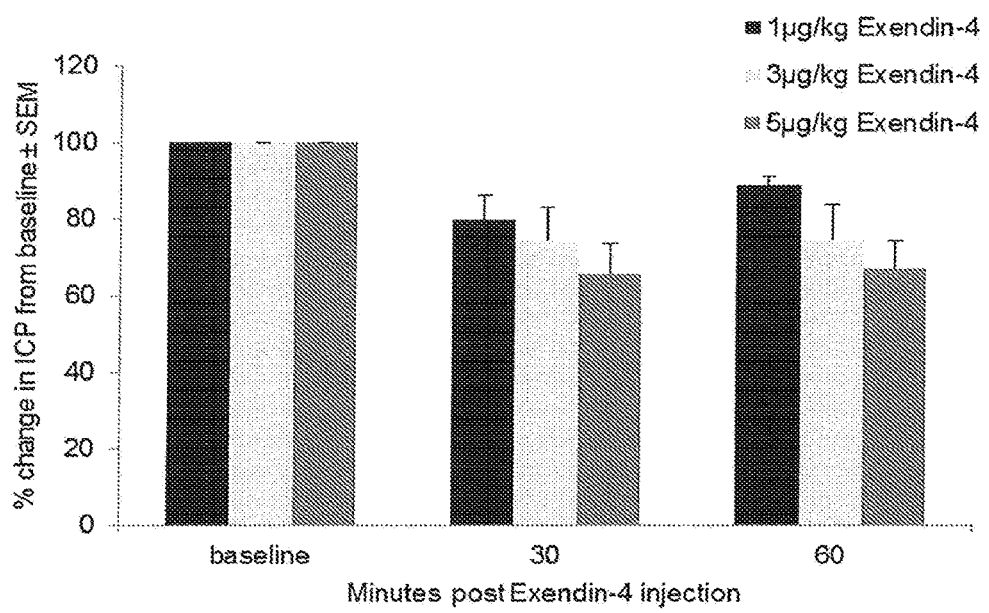
Figure 13:
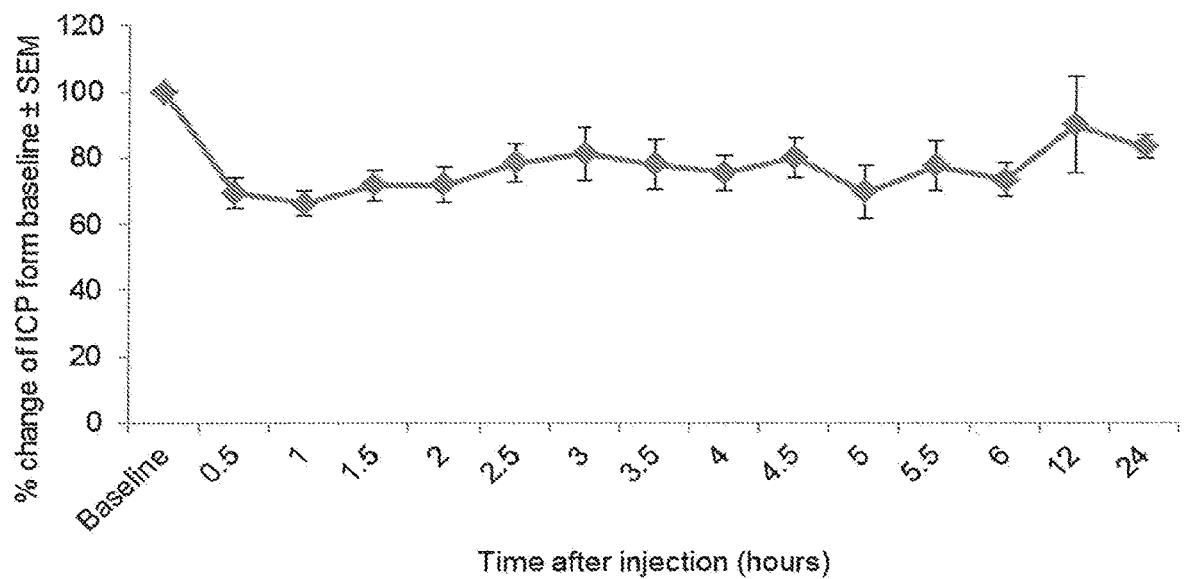

FIG. 9 shows the change in GLP-1R in CPe cells compared to the choroid plexus explants. (A) The histogram represents the mean±SEM of the fold change in GLP-1R mRNA from the choroid plexus explants to the CPe cells (B) is a western blot analysis of GLP-1R protein levels. Higher levels of GLP-1R mRNA and protein were shown in the CPe cells compared to the choroid plexus explants;

FIG. 10 shows the effect of Exendin-4 on cAMP levels and $Na^+K^+$-ATPase activity in CPe cells. (A) The histogram represents the fold change in cAMP levels compared to control. Forskolin was used as a positive control. Exendin-4 significantly increased the levels of cAMP in CPe cells compared to control. (B) $Na^+K^+$-ATPase activity was measured by determining the concentration of inorganic phosphate generated by the hydrolysis of ATP that was sensitive to ouabain (a $Na^+K^+$-ATPase inhibitor). In these studies primary rat CPe cells, grown as a monolayer on permeable membrane inserts, were treated for 30 minutes with aCSF (n=5) or 100 nM Exendin-4 (n=6), in the presence or absence of 1 mM Ouabain. The histogram represents the ouabain-sensitive $Na^+K^+$-ATPase activity±SEM (% change from control). Exendin-4 significantly (** $P<0.01$) reduced $Na^+K^+$-ATPase activity in the choroid plexus compared to the control;

FIG. 11 shows the effect of Exendin-4 on intracranial pressure (ICP) in conscious rats. Rats were fitted with an epidural ICP pressure bolt 2 days prior to ICP measurements. A baseline was recorded before the rats received a subcutaneous injection of either saline (n=6) or 20 μg/kg Exendin-4 (n=7). (A) ICP traces of saline (blue) and Exendin-4 (red) treatment. Spikes in the trace represent when the animal is moving (*) and correct recording of ICP was determined by the response to jugular vein compression. (B) Line graph showing the percentage change from baseline±SEM after treatment with either saline or Exendin-4 measured every 5 minutes for 60 minutes. Exendin-4 significantly lowered the pressure compared to saline within 10 minutes of treatment and lasted for the full 60 minutes.  $P<0.01$, ** $P<0.0001$;

FIG. 12 is a histogram showing the effect of low doses of Exendin-4 on ICP. ICP recordings were made of the baseline ICP, 30 and 60 minutes after treatment. The histogram shows the percentage change in ICP from baseline±SEM with 1 μg/kg (n=4), 3 μg/kg (n=5) and 5 μg/kg (n=4) Exendin-4 at 30 minutes and 60 minutes post treatment; and FIG. 13 is a line graph showing the effect of low doses of Exendin-4 on ICP over a 24 hour period. The graph shows the percentage change from baseline±SEM after treatment with 5 μg/kg Exendin-4 measured over a period of 24 hours.

EXAMPLE 1

Disordered CSF dynamics underlies the aetiology of IIH. Choroid plexus (CP) secretion of CSF is a key factor in ICP regulation and is controlled by a number of ion channels, principally the basal $Na^+/H^+$ exchanger (10) which drives sodium transport $(Na)^+$ into the CP epithelium and is the rate limiting step for the apical $Na^+K^+$-ATPase pump which pumps $Na^+$ into the ventricles, creating an osmotic gradient to drive water into the CSF (11,12). CSF secretion is totally inhibited by ouabain, a $Na^+K^+$-ATPase inhibitor, and significantly reduced by inhibition of the $Na^+/H^+$ exchanger (10; 13-15). There is a scarcity of research into the mechanisms that control CSF secretion.

The incretins, principally glucagon like peptide-1 (GLP-1) and glucose-dependent insulinotropic polypeptide (GIP) are predominantly secreted from the distal small intestine in response to a meal. GLP-1 [GLP-1 (7-37)] is a 30 aminoacid hormone peptide produced by posttranslational processing of proglucagon in the L cells of the distal gut and alpha cells in the pancreas and nucleus of the solitary tract in the brain stem. GLP-1, which stimulates insulin release and proliferation of pancreatic beta cells, reduces blood glucose in diabetics and also promotes satiety and weight loss (9;16). Active GLP-1 is rapidly broken down (half-life<3 minutes) by dipeptidyl peptidase-4 (DPP-4) to its inactive metabolites. Therapeutic strategies include inhibitors of DDP-4 or GLP-1 agonists (e.g. Liraglutide and Exendin-4) and are currently in use to treat diabetes and obesity.

While the effects of incretins are known to be reduced in obese, non-diabetic patients (17), there is debate as to whether this is due to impaired activity or reduced levels of GLP-1 secretion. A number of studies have found lower levels of GLP-1 post meal stimulation in the obese (18;19) and a negative correlation with weight (17). Following weight loss GLP-1 levels measured over 3 hours partially recover (19). Incretin therapies are also associated with, and used therapeutically to drive weight loss (9)

GLP-1 signals centrally mainly through GLP-1R, a G-coupled protein receptor expressed in selected cell types within the pituitary gland, hypothalamus, hippocampus, olfactory cortex, circumventricular organs and interestingly the choroid plexus (19). GLP-1 crosses the blood brain barrier (20), however, the pathways by which gut secreted GLP-1 exerts central effects are debated: 1) binding to vagal afferents, or 2) via the blood brain barrier (21) (FIG. 1). The vagus nerve can also stimulate GLP-1 production at the nucleus tractus solitarius with a dense and widespread network of GLP-1 fibres reaching the ventricles and CSF (22).

Relevant to the present invention is the finding that GLP-1 has effects on renal sodium secretion, reducing sodium resorption and increasing diuresis (23-26). GLP-1 mediates the majority of its actions via its specific receptor (GLP-1R) (27), activation of which stimulates cAMP (28). In the kidney proximal tubule, GLP-1 has been shown to act via a protein kinase A (PKA) dependent mechanism which significantly reduces sodium resorption at the $N^+/H^+$ exchanger (29;30). Diuretic actions of incretins have led to the suggestion of their use as antihypertensive agents (30) and a number of active clinical trials are studying this (ClinicalTrials.gov Identifier; NCT01755572 and NCT00696982). Of interest is the role of inflammation in modulating the renal incretin system (3;31;32).

Choroid plexus generation of CSF is driven by epithelial sodium secretion by the $Na^+/K^+$ATPase in a mechanism analogous to that of an inverted renal proximal tubule. We suggest that akin to the renal incretin modulation of diuresis and sodium absorption, choroid plexus sodium secretion may also be modulated by incretins. We suggest that GLP-1 receptor activation, with the consequent intracellular increase in cAMP and PKA which in turn phosphorylates and consequently inhibits the basal $N^+/H^+$ exchanger and thus impeding the $Na^+K^+$ATPase generation of CSF (FIG. 2). In support of this, data is provided which demonstrates that exendin-4 (a GLP-1 analogue) can reduce intracellular sodium, potentially through inhibition of the $N^+/H^+$ exchanger (FIG. 3). We also show the co-localisation of expression of GLP-1R and $Na^+K^+$ATPase in the choroid plexus—see FIG. 4. Interestingly, we note clinically beneficial effects on ICP in IIH patients treated with diuretics such as furosemide. Treatment of choroid plexus explants with a GLP-1 agonist, exendin-4, resulted in stimulation of the GLP-1 receptor and increased levels of cAMP (see FIGS. 5 and 6), which support the hypothesis of how the agents of the present invention may function to result in a decrease in elevated ICP through a reduction in CSF production by choroid plexus cells.

Incretins, such as GLP-1, GLP-1 agonists and/or DPP IV inhibitors can be tested for their potential use in treating elevated ICP. Direct evaluation of ICP can be assessed by LP. LP measures of CSF pressure are, however, limited as they only reflect a snap shot of CSF pressure, which is known to vary diurnally. The non-invasive imaging technique, MR elastography (MRE) provides an indication of ICP based on brain compliance. Compliance assesses the stiffness of the brain tissue (33). Consequently elevated ICP reflects increased stiffness (34). It is based on mechanical vibrations of the brain through an external driver and detection of brain motion in synchrony with an external driver. This technique was originally developed to detect increased compliance as a marker of liver fibrosis. This non-invasive technique can directly assess the biomechanics of the brain tissue and provide an overall indication of brain compliance a marker of ICP (35;36). The results are more analogous to that of a CSF infusion test (a useful but invasive test to monitor ICP in IIH) and thus a valuable marker of ICP. Imaging can be conducted on an MRI and images analysed and interpreted.

Direct assessment of CSF secretion rate is not possible. However, it is possible to use a bioassay which measures the rate of CSF secretion in a functional cell culture model of CSF secretion using primary human choroid plexus epithelial (CPe) cells (ScienCell Research Laboratories, San Diego, USA). Cells are grown in a monolayer on a filter membrane support creating a functional barrier for modelling CSF secretion ((38). The bioassay can be validated through confirmation of barrier functionality (trans-epithelial electrical resistance (TEER) and identification of junctional proteins by immunohistochemistry). Further validation through incubation with GLP-1 (or exendin-4, a GLP-1 receptor agonist), exendin 9-39 (a GLP-1 receptor antagonist) and Ouabain/Acetazolamide (inhibitors of CSF secretion) can be conducted. CSF secretion rate can be quantified by the change in luminosity of FITC-dextran over time. FITC-dextran (67 kDa) can be added to either side of the cell monolayer (apical and basolateral chambers). As it is impermeable to the cell monolayer, any changes in fluorescence in the apical chamber would be due to fluid secretion by the monolayer into the apical chamber (38).

EXAMPLE 2

In the present study we used in vitro models to assess the localisation and distribution of the GLP-1R in the choroid plexus and determine the effects of GLP-1R stimulation on CSF secretion. Furthermore, we conducted in vivo studies to evaluate the effects of GLP-1 agonists on ICP. By exploring the role of GLP-1 in ICP regulation we may determine a novel therapeutic target for the treatment of IIH and other conditions characterised by raised ICP.

Materials and Methods
Reagents

Exendin-4 (GLP-1R agonist), Exendin fragment (Exendin-9, GLP-1R antagonist), Ouabain (specific $Na^+K^+$ATPase inhibitor), 3-Isobutyl-1-methylxanthine (IBMX; phosphodiesterase inhibitor) and Forskolin (adenylate cyclase activator) were purchased from Sigma-Aldrich. The myristoylated protein kinase inhibitor (PKI)-(14-22)-amide (protein kinase A [PKA] inhibitor) was purchased from Merck Chemicals. Primary antibodies for GLP-1R protein detection and localisation, and choroid plexus epithelial (CPe) cell characterisation included antibodies against GLP-1R (rabbit, ab39072, Abcam), transthyretin (TTR; sheep, ab9015, Abcam), $Na^+K^+$ATPase (rabbit, ab76020, Abcam), zona occludens-1 (ZO-1; rabbit, 61-7300, Life Technologies), aquaporin 1 (AQP1; rabbit, AB3065, Abcam) and β-actin (mouse, A5441, Sigma Aldrich). For immunohistochemistry, the Alexa Fluor® labelled secondary antibodies were purchased from Life Technologies and for western blot, a HRP-conjugated secondary antibody was bought from Cell Signalling Technology. Cell culture reagents were from Life Technologies or Sigma-Aldrich and unless specified all other chemicals were purchased from Sigma-Aldrich. For surgical procedures the midazolam was purchased from B. Braun and the fluanisone and fentanylcitrate from the Danish pharmacy supply.

Experimental Animals

For the in vitro work, 150-200 g female Sprague-Dawley rats (Charles River) were used at the University of Birmingham in accordance with the Animals and Scientific Procedures Act 1986, licensed by the UK Home Office and approved by the University of Birmingham Ethics Committee. For the in vivo studies, which were conducted in Rigshospitalet-Glostrup, 200-300 g female Sprague-Dawley rats (Taconic) were housed in groups of 4, kept under a 12 hour light/dark cycle with free access to food and water. All experimental procedures were approved by the Danish Animal Experiments Inspectorate (license number 2014-15-0201-00256). After treatments and surgical procedures rats were monitored daily for any adverse effects (i.e. piloerection, severe weight loss, porphyrin rings around the eyes and abnormal behaviour). Only one rat had to be euthanised due to post-operative CNS infection (saline group).

Primary CPe Cell Culture

Choroid plexus tissue from lateral and fourth ventricles were dissected and incubated with 0.25% trypsin solution for 2.5 hours at 4° C. followed by 30 minutes at 37° C. Trypsin digestion was stopped by the addition of newborn calf serum and the cell suspension was centrifuged at 20 g for 10 minutes. Cells were resuspended in DMEM/F12 supplemented with 10% FBS, 1% penicillin/streptomycin, 4 mM L-glutamine, 200 ng/ml hydrocortisone, 5 ng/ml sodium selenite and 10 ng/ml EGF. 20 µM cytosine arabinoside was used for the first 4 days in culture to limit the growth of fibroblasts (Gath et al., 1997). Initially the cells were seeded onto a laminin coated 6 well plate and allowed to grow for 2 days before being transferred to laminin coated 96 well plates or 12 well inserts (Greiner Bio-One Ltd). On day 4 the media was replaced with DMEM/F12 supplemented with 10% FBS and 1% penicillin/streptomycin and changed every 2-3 days. After reaching confluency, CPe cells were serum deprived for 3 days prior to the beginning of the studies (between days 10-14).

Choroid Plexus Explants

The choroid plexus from the lateral ventricles were dissected and placed in artificial CSF (aCSF; 118 mM NaCl, 22 mM $NaHCO_3$, 1.45 mM $K_2HPO_4$, 1 mM $MgSO_4$, 1 mM $CaCl_2$ and 10 mM glucose). To evaluate the effects of Exendin-4 on GLP-1R localisation within the cell, the explants were incubated with aCSF containing 100 nM Exendin-9 for 15 minutes or 100 nM Exendin-4 for 15 and 30 minutes. The explants were then fixed and stained following the protocol described below. To determine the effects of Exendin-4 on GLP-1R mRNA expression and protein levels the explants were incubated with aCSF containing 100 nM Exendin-4 for 3 and 6 hours, immediately frozen in liquid nitrogen and stored at −80° C.

Immunofluorescent Staining

For staining of rat brain tissue sections, rats were killed and immediately perfused transcardially with 10 mM PBS, pH 7.4 (PBS) followed by 4% paraformaldehyde (Alfa Aesar) in PBS. Brains were postfixed overnight at 4° C., cryoprotected by sequential immersion in 10%, 20% and 30% sucrose in PBS at 4° C., embedded in OCT (Fisher Scientific), and 15-µm-thick coronal sections cut on a cryostat (Bright Instruments), mounted on charged microscope slides and stored at −20° C. until use. Sections were first washed in PBST (PBS containing 0.3% Tween20), blocked in PBST containing 2% bovine serum albumin (BSA) and 15% normal goat serum (NGS) for 20 minutes at room temperature, and then incubated with the primary antibody (PBST with 2% BSA) at 4° C. overnight. After washing in PBST, sections were incubated for 1 hour at room temperature in the dark with the appropriate Alexa Fluor 488 labelled secondary antibody diluted in PBST containing 2% BSA and 1.5% NGS. Finally, sections were washed in PBST before mounting in Vectashield containing the nuclear stain DAPI (Vector Laboratories).

For fluorescence labelling of choroid plexus explants and CPe cells, cells were first fixed in PBS containing 2% PFA and 2% glucose for 20 minutes at room temperature, washed in PBS and then permeabilised with methanol for 6 minutes at room temperature. The cells were stained using the same technique described above except that PBST was substituted with PBS.

Stained cells and sections were viewed under a Zeiss LSM 510 UV-confocal microscope (Carl Zeiss) and multiple Z-stack images were taken.

Quantitative Polymerase Chain Reaction (qPCR)

For qPCR studies, hypothalamus, anterior pituitary and choroid plexus were dissected, immediately frozen in liquid nitrogen and stored at −80° C. Primary cultures of CPe cells were grown on 12 well inserts until confluency. Total RNA was extracted using the GenElute mammalian total RNA extraction kit (Sigma-Aldrich) and carried out according to the manufacturer's instructions. RNA was reverse transcribed to complementary DNA (cDNA) using a high capacity reverse transcription kit according to the manufacturer's protocol (Life Technologies). Taqman Gene Expression Assays (Life Technologies) were used to assess the expression of GLP-1R (assay number Rn00562406_m1). The 18S ribosomal subunit was used as an endogenous reference (4319413E) and samples were run in triplicate. The cycle number at which the particular sample crossed that threshold (Ct) was used to determine the levels of gene expression and ΔCt was calculated as the difference between the Ct (gene of interest) and the Ct (endogenous reference).

Western Blot

The hypothalamus, pituitary and choroid plexus were dissected, immediately frozen in liquid nitrogen and stored at −80° C. Tissues were homogenised in ice cold lysis buffer (20 mM Tris-HCl pH 7.4, 150 mM NaCl, 1 mM EDTA, 0.5 mM EGTA, 1% NP-40 containing protease inhibitor) and centrifuged at 13,000 g to remove cell debris. CPe cells were grown on 12 well inserts until confluency. Cell and tissue lysates (3 µg protein) were separated on an 8% SDS-PAGE gel. The proteins were transferred onto a polyvinylidene difluoride (PVDF) membrane and subsequently blocked with 5% skimmed milk powder in TBST (TBS pH 7.4 with 0.5% Tween20) for 1 hour at room temperature before incubation with the GLP-1R or β-actin antibodies diluted in milk/TBST overnight at 4° C. After washing in TBST the membranes were incubated with HRP-conjugated secondary antibody diluted in milk/TBST for 1 hour at room temperature. The bands were detected using ECL reagents (Amersham) and developed onto film.

cAMP Assay

The effect of Exendin-4 on the downstream GLP-1R signalling pathway was assessed by measuring the levels of cAMP in CPe cells using the Amersham cAMP Biotrak Enzyme immunoassay (EIA) System (RPN 225, GE Healthcare Life Sciences). CPe cells were grown on a 96 well plate and on the day of the experiment incubated in aCSF supplemented with 1 mM IBMX containing; 100 nM Exendin-4 (n=8) or 100 nM Forskolin (positive control; n=5) for 30 minutes at 37° C. The cells were subsequently lysed and cAMP detected according to the manufacturer's instructions.

$Na^+K^+$ATPase Activity Assay

The effect of Exendin-4 on $Na^+K^+$ATPase activity in the choroid plexus was evaluated by the colorimetric measurement of phosphate released from ATP with the use of a phosphate assay kit (ab65622, Abcam); with $Na^+K^+$ATPase activity being defined as the portion of phosphate produced that is sensitive to Ouabain. CPe cells were incubated with aCSF for 1 hour at 37° C. before incubation in aCSF containing; 100 nM Exendin-4 (n=7), 5 µM PKI-16-22-amide (n=8), 100 nM Exendin-4+5 µM PKI-16-22-amide (n=8); in the presence and absence of 1 mM Ouabain for 30 minutes at 37° C. The cells were then lysed on ice and spun at 13,000 g to remove cell debris. Phosphate was measured as per the manufacturer's instructions. Briefly the samples were added to the reaction mix and incubated at room temperature for 60 minutes before the plate was read at 690 nm. $Na^+K^+$ATPase activity was calculated as the difference between the amount of phosphate produced in the presence and absence of Ouabain for each treatment.

Implantation of an Epidural Pressure Bolt

This procedure and its validation were recently published as a methodological work and contains all technical and surgical detail (Uldall et al, 2014). In brief, rats were anaesthetised (2.7 ml/kg subcutaneous injection containing 1.25 mg/ml midazolam, 2.5 mg/ml fluanisone and 0.079 mg/ml fentanylcitrate). The rat was placed in a stereotactic frame (David Kopf Instruments) and a 2 cm-midline incision was performed on top of the skull and the bone was exposed by retracting the skin and soft tissue. A dental drill was used to induce 4 burr holes in the skull; one large hole was carefully drilled to expose the dura mater to enable placement of the epidural pressure bolt (C313G-3UP, PlasticsOne), with the cannula cut to be level with the base of the pedestal. The other 3 smaller holes were used to fit anchoring screws to the skull. The epidural pressure bolt and the anchoring screws were placed and aligned with the interior surface of the skull and secured using dental resin-cement (Clearfil SA Cement, RH Dental). The epidural pressure bolt and the transducer (DTX-Plus™, Argon Medical Devices) were then connected by a polyethylene tube filled with sterile water, ensuring the absence of air bubbles.

The pressure signal was visualised and recorded using Perisoft v.2.5.5 (Perimed). Correct ICP signal was confirmed by the transient elevation of ICP after jugular vein compression. When the ICP recording procedure was completed the epidural pressure bolt was closed with a bite proof cap (303DCFTX2, PlasticsOne) and the rat allowed to recover.

ICP Recordings and Exendin-4 Treatment

In order to perform recordings in conscious animals, rats were sedated with midazolam (2.5 mg/kg subcutaneous injection) and the transducer connected to the epidural pressure bolt. The rat was then placed in an infusion cage (Instech Laboratories), which had a swirl lever arm to ensure unhindered movement. The ICP signal was again confirmed by jugular vein compression as described above. A stable baseline ICP reading was recorded for 30 minutes before the rats received a 0.5 ml subcutaneous injection of either saline (n=6) or Exendin-4 (20 µg/kg; n=7). ICP was recorded for a further 60 minutes.

Statistical Analysis

Values were represented as mean and standard error of the mean (SEM). The data was analysed using GraphPad Prism software. Non-parametric Kruskall-Wallis testing was used for comparisons between 3 or more groups (qPCR experiments, western blot analyses, cAMP levels, phosphate assay), and was followed by non-parametric Mann-Whitney test (two-tailed) with the appropriate adjustment for multiple comparisons (Bonferroni). Two-way ANOVA was used for the comparison of ICP between two groups over a period of time. Values were considered statistically significant when P-values were *$P<0.05$, $P<0.01$, *$P<0.001$, ****$P<0.0001$.

Results

GLP-1R mRNA Expression and Protein Levels in the Choroid Plexus

GLP-1R mRNA expression and protein levels were determined in choroid plexus explants and compared to GLP-1R positive brain tissues. As expected, GLP-1R mRNA expression was present in high levels in the hypothalamus and only low levels in the pituitary (FIG. 7A). GLP-1R mRNA was expressed in the choroid plexus. Results from western blot analyses of choroid plexus explants supported these findings and demonstrated the presence of a single 53 kDa band corresponding to the expected molecular weight for GLP-1R (FIG. 7B).

The Effect of Exendin-4 on GLP-1R Localisation, mRNA Expression and Protein Levels In order to determine the cellular distribution of GLP-1R in the choroid plexus and the effect of Exendin-4 (GLP-1R agonist) and Exendin-9 (GLP-1R competitive antagonist that restricts GLP-1R internalisation) treatment, choroid plexus explants were immunostained with a specific antibody to GLP-1R. GLP-1R positive staining was localised predominantly within the cytoplasm, as well as on the apical surface and in cell to cell contacts of the CPe cells. After both Exendin-9 and Exendin-4 treatment for 15 minutes, the receptor was predominantly restricted to the apical surface of the CPe cells with minimal cytoplasmic staining detected. Furthermore, after 30 minutes of Exendin-4 treatment most of the GLP-1R positive staining had translocated back to the cytoplasm and could also be observed on the basolateral side of the CPe cells.

Treatment with Exendin-4 for 3 hours showed significant increases ($P<0.05$) in the levels of GLP-1R mRNA and protein in choroid plexus explants compared to aCSF (FIG. 8A-B). After 6 hours of Exendin-4 treatment, GLP-1R mRNA had returned to basal levels however GLP-1R protein still remained high.

Characterisation of Primary CPe Cell Cultures

To further investigate the role of GLP-1R in the choroid plexus, CPe cells were isolated and grown in culture. To confirm the identity of the primary CPe cells they were characterised using antibodies against specific proteins known to be present in CPe cells and then compared to CPe cells in vivo. Transthyretin (TTR), a transporter of thyroxine and retinol A that specifically localises to CPe cells was detected in both the choroid plexus and cultured CPe cells. TTR was present within the cytoplasm, with more intense staining in the perinuclear area. $Na^+K^+ATPase$, the main driver of $Na^+$ transport from the CPe cells into the CSF, was localised to the apical surface of the choroid plexus and cultured CPe cells. The tight junction protein, ZO-1 was detected in the epithelial cells of the choroid plexus tissue and was clearly detected in cell to cell contacts in vitro. AQP1 positive staining was present on the apical surface of the CPe cells in vivo, a similar pattern to that of the $Na^+K^+ATPase$. It is interesting to note that in vitro, the intensity of cell surface AQP1 immunostaining was not homogenous with some cells showing a higher intensity of staining compared to others. The GLP-1R was observed mainly in the cytoplasm and apical surface of the CPe cells in vivo and in vitro. GLP-1R mRNA and protein were also expressed in the CPe cells and was higher than in the whole tissue choroid plexus explants (FIG. 9).

The Effect of Exendin-4 on cAMP Levels and $Na^+K^+$ ATPase Activity

To investigate the effects of Exendin-4 on GLP-1R activation in the choroid plexus, the levels of cAMP, were assessed in CPe cell cultures. Treatment with Exendin-4 lead to a 2 fold increase in cAMP, which was significantly different ($P<0.01$) compared to baseline (FIG. 10A).

To investigate the role of the GLP-1R signalling pathway on CSF secretion, $Na^+K^+ATPase$ activity (a marker of CSF secretion) was assessed in CPe cell cultures. Exendin-4 treatment significantly reduced ($P<0.05$) the levels of $Na^+K^+$ ATPase specific phosphate production (39.3±9.4% of control) compared to the control (FIG. 10B). In addition, a PKA inhibitor was able to abolish the Exendin-4 reduction in $Na^+K^+ATPase$ activity.

Exendin-4 Treatment Reduces ICP in Conscious Rats

To establish whether GLP-1 agonists were able to modulate ICP, the ICP was measured before and after a subcutaneous injection of either saline or Exendin-4 in conscious healthy adult rats. ICP recordings made before the injection were to establish a baseline, followed by continuous recording to 60 minutes after the injection. Examples of the traces are shown in FIG. 11A. Within 10 minutes of the subcutaneous injection of Exendin-4, ICP was significantly reduced compared to rats treated with saline (reduction from baseline of 60.6±4.9% (p<0.0001)) (FIG. 11B). Furthermore, ICP remained significantly lower for the rest of the recording (60 minutes) with the largest decrease in ICP being 58.3±SD 5.0% of baseline (at 35 minutes post injection).

ICP recordings were made of the baseline ICP 30 and 60 minutes after treatment with 1 µg/kg (n=4), 3 µg/kg (n=5) and 5 µg/kg (n=4). As shown in FIG. 12, all three doses of Exendin-4 lowered the ICP from baseline, with 5 µg/kg showing the greatest reduction. Additionally, at 5 µg/kg the ICP remained reduced over a 24 hour period (FIG. 13).

Discussion

It has been demonstrated for the first time that the GLP-1R agonist Exendin-4 is able to reduce ICP in conscious rats. The results described above suggest that the ICP lowering properties of Exendin-4 occur through reduced CSF secretion at the choroid plexus, demonstrated by the reduction in $Na^+K^+ATPase$ activity in CPe cells. Exendin-4 modulation of CSF production is thought to act through the GLP-1R/cAMP/PKA signalling pathway.

The above data supports the hypothesis that molecules, including integrins, such as GLP-1, GLP-1 antagonists and/or DPP IV inhibitors can be of use in reducing ICP in patients with IIH and/or other conditions associated with ICP.

REFERENCES (1) Corbett J J, Savino P J, Thompson H S, Kansu T, Schatz N J, Orr L S et al. Visual-Loss in Pseudo-Tumor Cerebri—Follow-Up of 57 Patients from 5 to 41 Years and A Profile of 14 Patients with Permanent Severe Visual-Loss. Archives of Neurology 1982; 39(8): 461-74.
(2) World Health Organization. Global Database on Body Mass Index. 2013. 19-9-0013. Ref Type: Online Source
(3) Sinclair A J, Ball A K, Burdon M A, Clarke C E, Stewart P M, Cumow S J et al. Exploring the pathogenesis of IIH: An inflammatory perspective. Journal of Neuroimmunology 2008; 201:212-20.
(4) Lueck C, McIlwaine G. Interventions for idiopathic intracranial hypertension. Cochrane Database of Systematic Reviews 2005; (3).
(5) Ball A, Howman A. A randomised controlled trial of treatment for idiopathic intracranial hypertension. Journal of Neurology 2010; 1-8.
(6) Celebisoy N, Gokcay F, Sirin H, Akyurekli O. Treatment of idiopathic intracranial hypertension: topiramate vs acetazolamide, an open-label study. Acta Neurologica Scandinavica 2007; 116(5):322-7.
(7) Curry W T, Butler W E, Barker F G. Rapidly rising incidence of cerebrospinal fluid shunting procedures for idiopathic intracranial hypertension in the United States, 1988-2002. Neurosurgery 2005; 57(1):97-107.
(8) Sinclair A J, Kuruvath S, Sen D, Nightingale P G, Burdon M A, Flint G. Is cerebrospinal fluid shunting in idiopathic intracranial hypertension worthwhile? A 10-year review. Cephalalgia 2011; 31(16):1627-33.
(9) Astrup A, Rossner S, Van Goal L, Rissanen A, Niskanen L, Al Hakim M et al. Effects of liraglutide in the treatment of obesity: a randomised, double-blind, placebo-controlled study. Lancet 2009; 374(9701):1606-16.
(10) Murphy V A, Johanson C E. Alteration of Sodium-Transport by the Choroid-Plexus with Amiloride. Biochimica et Biophysica Acta 1989; 979(2):187-92.
(11) Amin M S, Reza E, Wang H, Leenen F H. Sodium Transport in the Choroid Plexus and Salt-Sensitive Hypertension. Hypertension 2009; 54(4):860-U359.
(12) Speake T, Whitwell C, Kajita H, Majid A, Brown P D. Mechanisms of CSF secretion by the choroid plexus. Microscopy Research and Technique 2001; 52(1):49-59.
(13) Dayson H, Segal M B. Effects of Some Inhibitors and Accelerators of Sodium Transport on Turnover of Na-22 in Cerebrospinal Fluid and Brain. Journal of Physiology-London 1970; 209(1):131-&.
(14) Welch K. Secretion of Cerebrospinal Fluid by Choroid Plexus of Rabbit. American Journal of Physiology 1963; 205(3):617-&.
(15) Zeuthen T, Wright E M. Electrogenic Na+-K+ Pump in Choroid-Plexus. Biochimica et Biophysica Acta 1978; 511(3):517-22.
(16) Campbell J E, Drucker D J. Pharmacology, Physiology, and Mechanisms of Incretin Hormone Action. Cell Metabolism 2013; 17(6):819-37.
(17) Muscelli E, Mari A, Casolaro A, Camastra S, Seghieri G, Gastaldelli A et al. Separate impact of obesity and glucose tolerance on the incretin effect in normal subjects and type 2 diabetic patients. Diabetes 2008; 57(5):1340-8.
(18) Carr R D, Larsen M O, Jelic K, Lindgren O, Vikman J, Holst J J et al. Secretion and Dipeptidyl Peptidase-4-Mediated Metabolism of Incretin Hormones after a Mixed Meal or Glucose Ingestion in Obese Compared to Lean, Nondiabetic Men. Journal of Clinical Endocrinology & Metabolism 2010; 95(2):872-8.
(19) Verdich C, Toubro S, Buemann B, Madsen J L, Holst J J, Astrup A. The role of postprandial releases of insulin and incretin hormones in meal-induced satiety—effect of obesity and weight reduction. International Journal of Obesity 2001; 25(8):1206-14.
(19) Alvarez E, Roncero I, Chowen J A, Thorens B, Blazquez E. Expression of the glucagon-like peptide-1 receptor gene in rat brain. Journal of Neurochemistry 1996; 66(3):920-7.
(20) Banks W A, During M J, Niehoff M L. Brain uptake of the glucagon-like peptide-1 antagonist exendin (9-39) after intranasal administration. Journal of Pharmacology and Experimental Therapeutics 2004; 309(2):469-75.
(21) Lockie S H. Glucagon-Like Peptide-1 Receptor in the Brain: Role in Neuroendocrine Control of Energy Metabolism and Treatment Target for Obesity. Journal of Neuroendocrinology 2013; 25(7):597-604.
(22) Larsen P J, TangChristensen M, Holst J J, Orskov C. Distribution of glucagon-like peptide-1 and other preproglucagon-derived peptides in the rat hypothalamus and brainstem. Neuroscience 1997; 77(1):257-70.
(23) Gutzwiller J P, Tschopp S, Bock A, Zehnder C E, Huber A R, Kreyenbuehl M et al. Glucagon-like peptide 1 induces natriuresis in healthy subjects and in insulin-resistant obese men. Journal of Clinical Endocrinology & Metabolism 2004; 89(6):3055-61.
(24) Gutzwiller J P, Hruz P, Huber A R, Hamel C, Zehnder C, Drewe J et al. Glucagon-like peptide-1 is involved in sodium and water homeostasis in humans. Digestion 2006; 73(2-3):142-50.
(25) TangChristensen M, Larsen P J, Goke R, FinkJensen A, Jessop D S, Moller M et al. Central administration of GLP-1-(7-36) amide inhibits food and water intake in rats. American Journal of Physiology-Regulatory Integrative and Comparative Physiology 1996; 271(4): R848-R856.
(26) von Websky K, Reichetzeder C, Hocher B. Physiology and pathophysiology of incretins in the kidney. Current Opinion in Nephrology and Hypertension 2014; 23(1): 54-60.
(27) Wei Y, Mojsov S. Tissue-Specific Expression of the Human Receptor for Glucagon-Like Peptide-I—Brain, Heart and Pancreatic Forms Have the Same Deduced Amino-Acid-Sequences. Febs Letters 1995; 358(3):219-24.
(28) Gallwitz B, Witt M, Folsch U R, Creutzfeldt W, Schmidt W E. Binding-Specificity and Signal-Transduction of Receptors for Glucagon-Like Peptide-1(7-36) Amide and Gastric-Inhibitory Polypeptide on Rinm5F Insulinoma Cells. Journal of Molecular Endocrinology 1993; 10(3):259-68.
(29) Carraro-Lacroix L R, Malnic G, Girardi A C C. Regulation of Na+/H+ exchanger NHE3 by glucagon-like peptide 1 receptor agonist exendin-4 in renal proximal tubule cells. American Journal of Physiology-Renal Physiology 2009; 297(6):F1647-F1655.
(30) Crajoinas R O, Oricchio F T, Pessoa T D, Pacheco B P, Lessa L M, Malnic G et al. Mechanisms mediating the diuretic and natriuretic actions of the incretin hormone glucagon-like peptide-1. American Journal of Physiology-Renal Physiology 2011; 301(2): F355-F363.
(31) Edwards L J, Sharrack B, Ismail A, Tench C R, Gran B, Dhungana S et al. Increased levels of interleukins 2 and 17 in the cerebrospinal fluid of patients with idiopathic intracranial hypertension. Am J Clin Exp Immunol 2013; 2(3):234-44.

(32) Stefanovic V, Ardaillou N, Vlahovic P, Placier S, Ronco P, Ardaillou R. Interferon-Gamma Induces Dipeptidylpeptidase-lv Expression in Human Glomerular Epithelial-Cells. Immunology 1993; 80(3):465-70.
(33) Schregel K, Wuerfel E, Garteiser P, Gemeinhardt I, Prozorovski T, Aktas 0 et al. Demyelination reduces brain parenchymal stiffness quantified in vivo by magnetic resonance elastography. Proc Natl Acad Sci USA 2012 Apr. 24; 109(17):6650-5.
(34) Alperin N, Ranganathan S, Bagci A, Adams D, Ertl-Wagner B, Saraf-Lavi E et al. MRI Evidence of Impaired CSF Homeostasis in Obesity-Associated Idiopathic Intracranial Hypertension. American Journal of Neuroradiology 2013; 34(1):29-34.
(35) Freimann F B, Streitberger K J, Klatt D, Lin K, McLaughlin J, Braun J et al. Alteration of brain viscoelasticity after shunt treatment in normal pressure hydrocephalus. Neuroradiology 2012 March; 54(3):189-96.
(36) Streitberger K J, Wiener E, Hoffmann J, Freimann F B, Klatt D, Braun J et al. In vivo viscoelastic properties of the brain in normal pressure hydrocephalus. NMR Biomed 2011 May; 24(4):385-92.
(37) Nakazato 2011; Development of the novel delivery system of GLP-1 administration for the treatment of diabetes mellitus. Japanese Journal of Clinical Medicine [2011, 69(5):918-922]
(38) Baehr, Reichel et al 2006: Choroid plexus epithelial monolayers—a cell culture model from porcine brain; Cerebrospinal Fluid Res. 2006; 3: 13; Pgs 1-14.
(39) Gath U, Hakvoort A, Wegener J, Decker S, Galla H J; Porcine choroid plexus cells in culture: expression of polarized phenotype, maintenance of barrier properties and apical secretion of CSF-components. Eur J Cell Biol. 1997 September; 74(1):68-78.
(40) Uldall M, Juhler M, Skjolding A D, Kruuse C, Jansen-Olesen I, Jensen R. A novel method for long-term monitoring of intracranial pressure in rats. J Neurosci Methods. 2014 Apr. 30; 227:1-9.

The invention claimed is:

1. A method of reducing elevated intracranial pressure (ICP) in a subject suffering from elevated ICP, the method comprising administering to the subject an agent selected from exendin-4 and Exenatide at a dose of at least 1 µg/kg to cause a reduction in elevated ICP in the subject, wherein a reduction occurs in the subject within 30 minutes of administration of the agent, and wherein the subject is a human.

2. The method according to claim 1, wherein a reduction occurs in the subject within 10 minutes of administration of the agent.

3. The method according to claim 1, wherein a reduction lasts for at least 60 minutes after administration of the agent.

4. The method according to claim 1, wherein the agent is Exenatide.

5. The method according to claim 1, wherein the administering of the agent results in a reduction in Na+ transport into choroid plexus epithelial cells from the blood which causes the reduction in production of cerebral spinal fluid.

6. The method according to claim 1, wherein the agent is administered via injection.

7. The method according to claim 6, wherein the injection is a subcutaneous injection.

8. The method according to claim 1, wherein the agent is administered to the subject at a dose of less than 10 µg/kg.

9. The method according to claim 1, wherein the elevated ICP to be treated is associated with idiopathic intracranial hypertension (IIH), secondary pseudotumour cerebri, hydrocephalus, normal pressure hydrocephalus, raised intracranial pressure secondary to brain tumour, meningitis, brain trauma, brain injury, or venous sinus thrombosis.

10. The method according to claim 1, wherein the elevated ICP to be treated is associated with idiopathic intracranial hypertension (IIH).

11. The method according to claim 1, wherein the agent is administered by at least daily administration.

12. The method according to claim 1, wherein the method further comprises administering at least one other therapeutic agent.

13. The method according to claim 12, wherein the at least one other therapeutic agent is selected from incretin, incretin receptor agonists and incretin enhancers.

14. The method according to claim 1, wherein the method further comprises administering at least one other therapeutic agent and the elevated ICP to be treated is associated with idiopathic intracranial hypertension (IIH).

15. The method according to claim 1, wherein the agent is Exenatide, the method further comprises administering at least one other therapeutic agent and the elevated ICP to be treated is associated with idiopathic intracranial hypertension (IIH).

16. The method according to claim 1, wherein the elevated ICP to be treated is associated with idiopathic intracranial hypertension (IIH) and the agent is Exenatide, wherein the Exenatide is administered via subcutaneous injection to the subject at a dose of less than 10 µg/kg by at least daily administration.

17. The method according to claim 1, wherein the method is a method of reducing elevated intracranial pressure (ICP) in a subject suffering from elevated ICP by reducing production of cerebral spinal fluid in the subject, the method comprising administering to the subject the agent in an amount sufficient to reduce production of cerebral spinal fluid in the subject and cause a reduction in elevated ICP in the subject, wherein a reduction occurs in the subject within 30 minutes of administration of the agent and a reduction lasts for at least 60 minutes after administration of the agent.

18. The method according to claim 17, wherein the elevated ICP to be treated is associated with idiopathic intracranial hypertension (IIH) and the agent is Exenatide, wherein the Exenatide is administered via subcutaneous injection to the subject at a dose of less than 10 µg/kg by at least daily administration.

19. The method according to claim 1, wherein the agent is administered to the subject at a dose of from 1 to 10 µg/kg.

20. The method according to claim 1, wherein the agent is administered to the subject at a dose of at least 5 µg/kg.

21. The method according to claim 1, wherein there is at least a 20% reduction in ICP from baseline within 30 minutes of administration of the agent.

22. The method according to claim 1, wherein the elevated ICP to be treated is associated with raised intracranial pressure secondary to brain trauma or brain injury.

* * * * *